(12) United States Patent
Maezawa

(10) Patent No.: US 11,206,900 B2
(45) Date of Patent: Dec. 28, 2021

(54) BODY WEIGHT MEASURING DEVICE AND BODY WEIGHT MEASURING SYSTEM

(71) Applicant: ZOZO, INC., Chiba (JP)

(72) Inventor: Yusaku Maezawa, Chiba (JP)

( * ) Notice: Subject to any disclaimer, the term of this patent is extended or adjusted under 35 U.S.C. 154(b) by 255 days.

(21) Appl. No.: 16/475,664

(22) PCT Filed: Dec. 8, 2017

(86) PCT No.: PCT/JP2017/044171
§ 371 (c)(1),
(2) Date: Jan. 30, 2020

(87) PCT Pub. No.: WO2018/128050
PCT Pub. Date: Jul. 12, 2018

(65) Prior Publication Data
US 2020/0205527 A1    Jul. 2, 2020

(30) Foreign Application Priority Data

Jan. 5, 2017   (JP) .............................. JP2017-000749

(51) Int. Cl.
*G01B 7/16*   (2006.01)
*A43D 1/02*   (2006.01)
*G01L 1/20*   (2006.01)

(52) U.S. Cl.
CPC .............. *A43D 1/027* (2013.01); *G01B 7/18* (2013.01); *G01L 1/205* (2013.01)

(58) Field of Classification Search
None
See application file for complete search history.

(56) References Cited

FOREIGN PATENT DOCUMENTS

| JP | 2002177015 | * | 5/2002 |
| JP | 2005192744 | * | 7/2005 |
| JP | 2015189776 | * | 11/2015 |

* cited by examiner

*Primary Examiner* — Lisa M Caputo
*Assistant Examiner* — Nigel H Plumb
(74) *Attorney, Agent, or Firm* — FisherBroyles, LLP; Rob L. Phillips

(57) ABSTRACT

A body measuring device configured to determine size and shape of a body portion of a user. The body measuring device incorporates a measuring sensor for measuring a physical change amount based upon a change in electrical characteristics wherein the measuring sensor is characterized by including at least either a pressure-type measuring sensor for measuring a pressure applied from the body of the user or an expansion-type measuring sensor for measuring a degree of expansion of a base member caused by the body shape of the user. This body measuring device configuration determines size and shape without a user needing to undertake any self-measurements.

16 Claims, 22 Drawing Sheets

Fig. 4
(a)
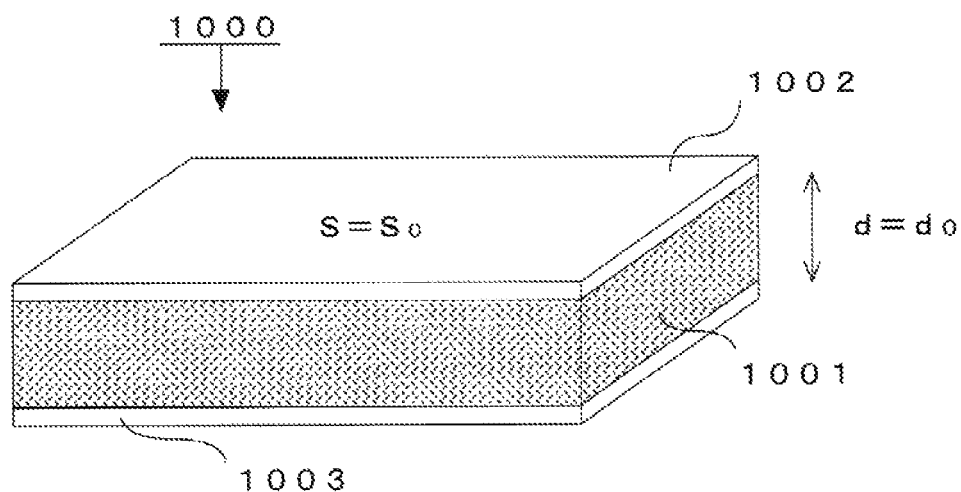
(b)
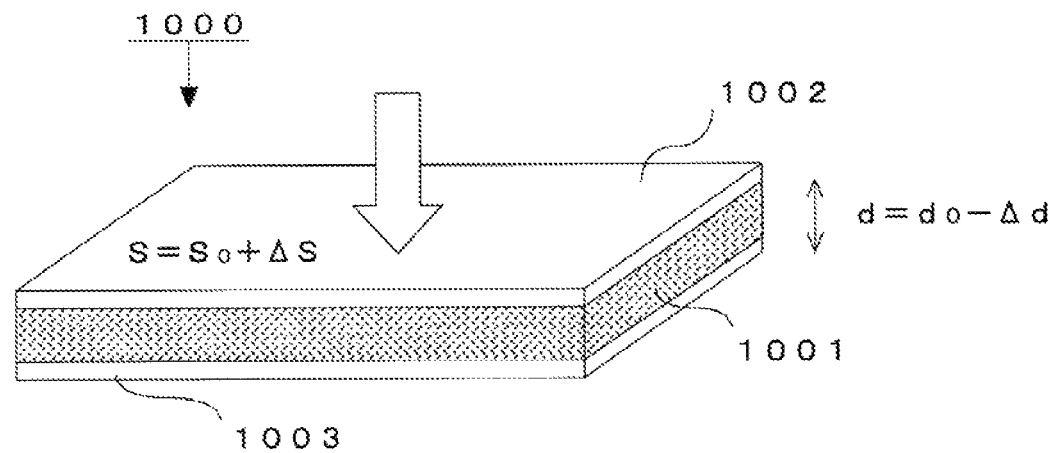

Fig. 6
(a)
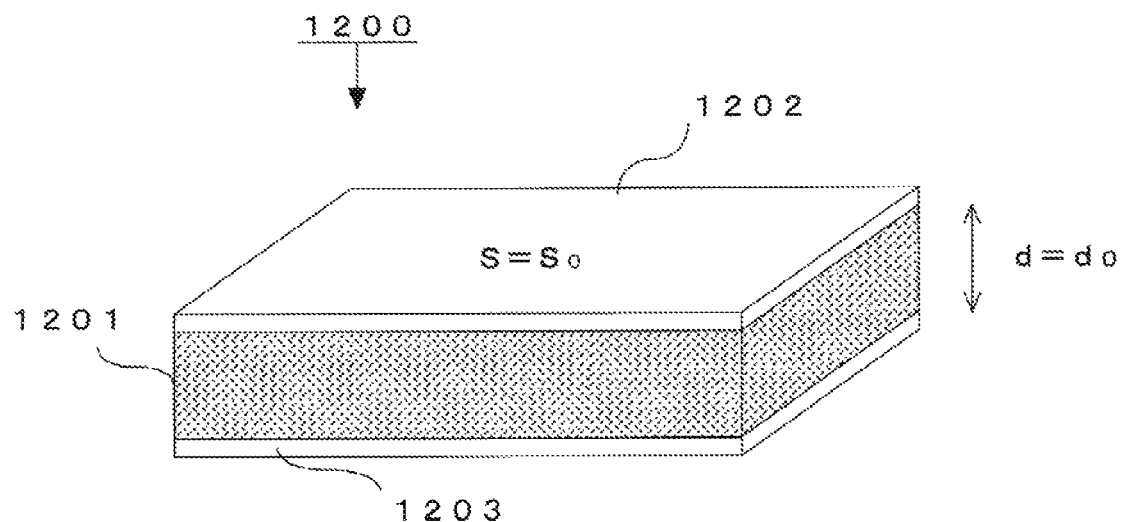
(b)
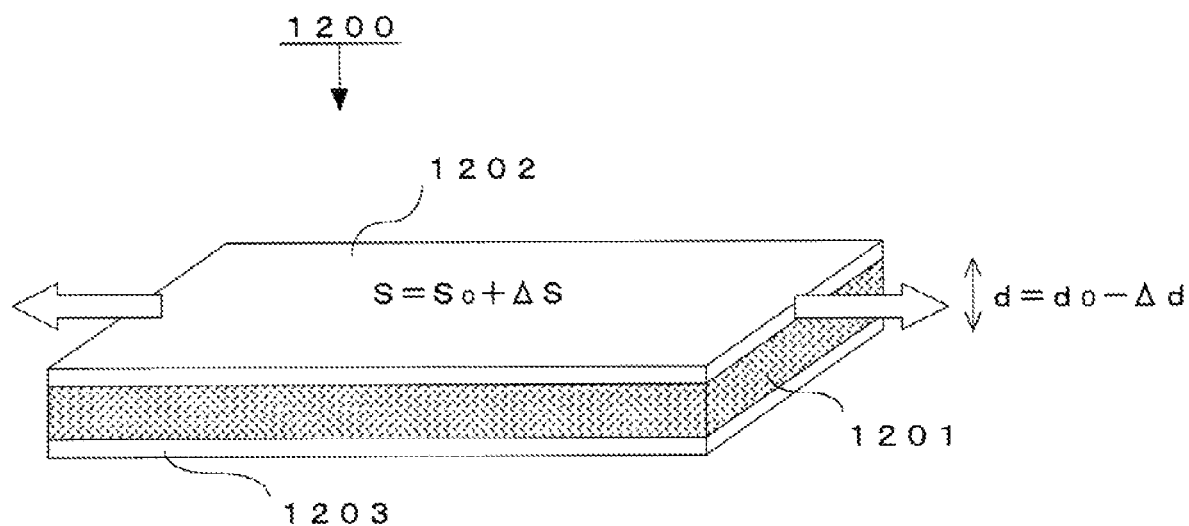

Fig. 16

USER MEASUREMENT DB 321

| USER ID | fd1 | fd2 | fd3 | fd4 | ... |
|---------|------|------|------|-----|-----|
| 0001 | 26.4 | 26.2 | 26.4 | 5.9 | ... |
| 0002 | 27.8 | 27.2 | 27.6 | 6.3 | ... |
| 0003 | 24.3 | 24.0 | 23.9 | 4.0 | ... |
| 0004 | 25.6 | 25.2 | 25.8 | 4.6 | ... |
| ... | ... | ... | ... | ... | ... |

Fig. 17

FOOTWEAR DB 322

| FOOTWEAR ID | fd1 | fd2 | fd3 | fd4 | ... |
|---|---|---|---|---|---|
| S0001 | 26.4 (26.0~26.8) | 26.2 (25.9~26.3) | 26.4 (26.0~26.5) | 5.9 (5.6~5.9) | ... |
| S0002 | 27.8 (27.5~27.9) | 27.2 (26.8~27.3) | 27.6 (27.0~28.2) | 6.3 (6.2~6.4) | ... |
| S0003 | 24.3 (24.0~24.5) | 24.0 (23.6~24.2) | 23.9 (23.6~23.9) | 4.0 (3.9~4.1) | ... |
| S0004 | 25.6 (25.3~25.7) | 25.2 (24.8~25.3) | 25.8 (25.5~25.9) | 4.6 (4.4~4.7) | ... |
| ... | ... | ... | ... | ... | ... |

Fig. 21
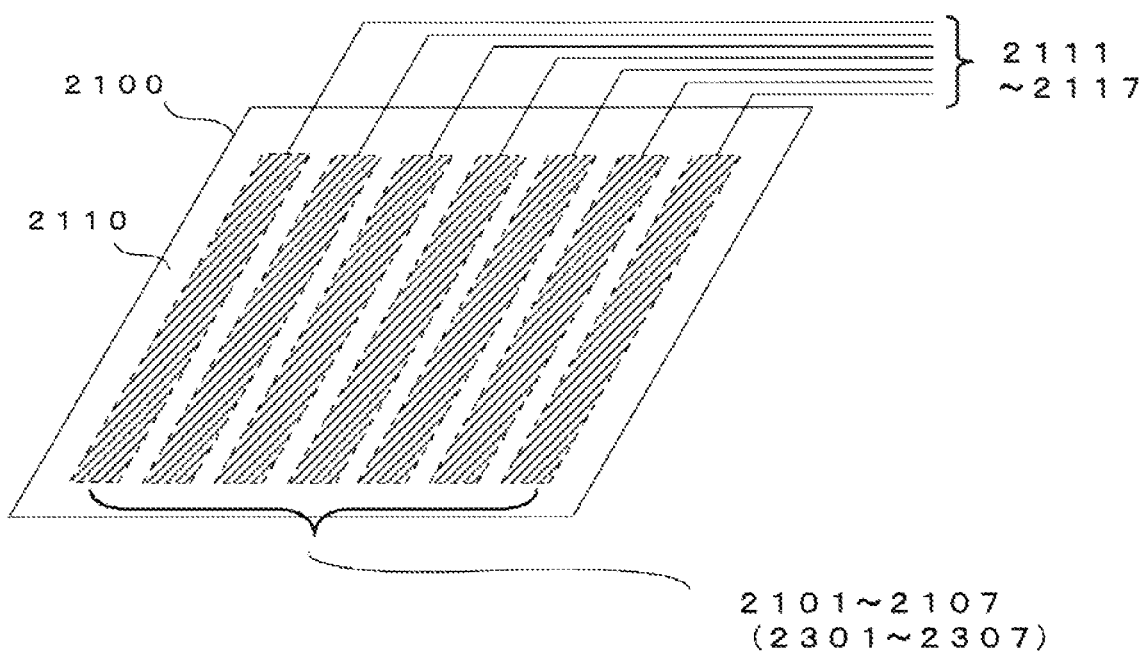
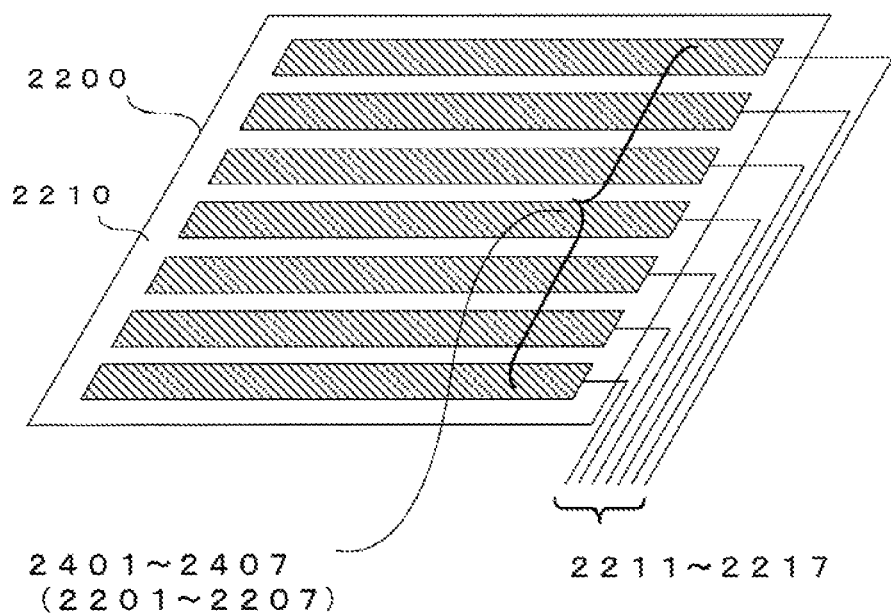

BODY WEIGHT MEASURING DEVICE AND BODY WEIGHT MEASURING SYSTEM

CROSS-REFERENCE TO RELATED APPLICATIONS

The present invention is filed under 35 U.S.C. § 371 as the U.S. national phase of International Patent Application No. PCT/JP2017/044171, filed Dec. 8, 2017, which designated the United States and which claims priority to Japanese Patent Application No. 2017-000749, filed Jan. 5, 2017, each of which is hereby incorporated in its entirety including all tables, figures, and claims.

TECHNICAL FIELD

The present invention relates to a body measuring device and a body measuring system, and in particular concerns such a body measuring device that is attached to a body of a user and measures a size or the like of the attached portion and a body measuring system thereof.

PRIOR ART

In recent years, because of the spread of Internet technologies, EC sites have come to deal with a wide variety of commodities, and the sales have been increasing rapidly.

Together with conveniences by which a user orders a commodity on the EC site by using a PC, a portable terminal or the like, and then the delivered commodity can be received at home without actually visiting the shop, the number of users are increasing greatly.

Among the above-mentioned EC sites, many of them deal with apparel commodities, such as clothes, hats, shoes and the like, and the number of users is close to reaching the number of actual stores.

However, upon purchasing the above-mentioned apparel commodities, it is sometimes unknown whether or not the corresponding commodity actually fits the size and shape of the user's body so that after the receipt of the commodity, the user tries it on, and when it does not fit the size or the like of his or her own body, he or she has to return the commodity and re-order another commodity of a different size.

In order to solve the above-mentioned problem, one of prior-art techniques has proposed a measuring kit for use in making shoes disclosed by Patent Document 1.

The measuring kit for use in making shoes disclosed by Patent Document 1 is provided with: as separated members, a foot type-taking device that has a movable member having no elasticity and receives a compressed load caused by a foot placed thereon, and then can form at least a concavo-convex pattern corresponding to a sole surface of the foot on its surface based upon a plastic deformation; a substrate which has at least a shape slightly expanded toward a front side in comparison with an external shape of the foot and on which the foot is placed; a heel stopper that is attached to a outer circumference of a rear portion of the substrate and capable of holding a heel of the foot by surrounding the heel thereof; a scale indication that is displayed on a front surface of the substrate and used for measuring a foot-length size of the foot; and a measuring device that is formed on a center of the substrate and capable of taking at least data about a circumferential height of a surface of the foot.

By using the measuring kit for use in making shoes of the above-mentioned Patent Document 1, the user can purchase custom-made shoes through mail order without visiting a worker at a shoes-manufacturing site.

PRIOR ART DOCUMENTS

Patent Documents

[Patent Document 1] JP-A No. 2012-217527

DETAILED DESCRIPTION OF THE INVENTION

Problems to be Solved by the Invention

However, in the case when the measuring kit for use in making shoes of the above-mentioned Patent Document 1 is used, since the general users lack a special size-taking technique, there are deviations in size-taking standard among the users in such points as to how to take a foot type and how to put a measure or the like, with the result that a problem is posed in that no size-taking process with high precision can be obtained.

Moreover, since after taking a foot type once, the foot type taking device maintains its shape, another problem is posed in that even when the size-taking process is not carried out properly or when the size of the corresponding person has changed by growth, it is impossible to again carry out the size-taking process.

The present invention has been devised to solve the above-mentioned problems, and an object of the present invention is to provide a body measuring device and a body measuring system that can be easily handled even by a user having no special size-taking technique, and are usable repeatedly.

Means for Solving Problems

In order to achieve the above-mentioned object, the present invention relates to a body measuring device which, when attached to a user, specifies a size and shape of an attached body portion of the user, and is provided with a measuring sensor for measuring a physical change amount based upon a change in electrical characteristics, and the measuring sensor is characterized by including at least either a pressure-type measuring sensor for measuring a pressure applied from the body of the user or an expansion-type measuring sensor for measuring a degree of expansion of a base member caused by the body shape of the user.

Moreover, the present invention relates to a body measuring device which, when attached to a user, specifies a size and shape of a foot of the user, and is provided with a measuring sensor for measuring a physical change amount based upon a change in electrical characteristics, and the measuring sensor is characterized by including a pressure-type measuring sensor for measuring a pressure applied from a sole of the user and an expansion-type measuring sensor for measuring a degree of expansion of a base member caused by the shape of the user's foot.

Moreover, the body measuring device relating to the present invention is formed into a footwear shape, and the pressure-type measuring sensor is disposed on a portion of a sole, and is characterized by measuring a pressure that is exerted on the sole of the user in a gravity direction.

Moreover, the body measuring device relating to the present invention is formed into a footwear shape, and the expansion-type measuring sensor is disposed on a toe portion of a sole, and is characterized by measuring a degree of expansion of the base member caused by a length of the toe of the user.

Moreover, the body measuring device relating to the present invention is formed into a footwear shape, and the expansion-type measuring sensor is disposed in a foot-surrounding direction, and is characterized by measuring a degree of expansion of the base member caused by the foot-surrounding length of the user.

Moreover, the body measuring device relating to the present invention is formed into a footwear shape, and the expansion-type measuring sensor is formed into an expandable belt shape, and is characterized in that a non-expandable member is coupled to a tip of the expansion-type measuring sensor so as to form a sole portion of a foot.

Moreover, the body measuring device relating to the present invention is formed into a footwear shape, and the expansion-type measuring sensor is formed into a belt shape expandable in a foot length direction, and is characterized in that non-expandable members are coupled to two ends in the foot length direction of the expansion-type measuring sensor so as to form a sole portion of a foot.

Moreover, in accordance with the body measuring device of the present invention, the pressure-type measuring sensor is provided with a pair of electrode substrates on which a plurality of plate-shape electrodes are disposed and a dielectric film disposed between the paired electrode substrates, and is characterized in that when a pressure is applied to the electrodes, a magnitude of a pressure applied from a sole can be specified based upon a change in electrostatic capacitance caused by the pressure.

Moreover, in accordance with the body measuring device of the present invention, the pressure-type measuring sensor is provided with a pair of electrode substrates on which a plurality of plate-shape electrodes are disposed substantially in parallel with one another and a pressure sensitive member containing a conductive substance, and the paired electrode substrates are disposed so as to allow the respective electrodes to be made face to face with each other so as to intersect with one another, and the pressure sensitive member coats the opposed surfaces of the paired electrode substrates so that when a pressure is applied to an intersecting portion of the electrodes, a magnitude of a pressure applied from the sole can be specified based upon a change in electric resistance value caused by the pressure.

Moreover, in accordance with the body measuring device of the present invention, the expansion-type measuring sensor is provided with a pair of plate-shape electrodes and a dielectric film disposed between the paired electrodes and is characterized in that when a tension is applied to the electrode so as to be expanded, a degree of expansion of the electrodes caused by the shape of the user's body is specified based upon a change in electrostatic capacitance caused by the expansion of the electrodes.

Moreover, in accordance with the body measuring device of the present invention, the expansion-type measuring sensor is provided with a plate-shape electrode having expandability, and is characterized in that when expanded upon application of a tension onto the electrode, the degree of expansion of the electrode caused by the shape of the user's body can be specified based upon a change in electrical resistance value caused by the expansion of the electrode.

Moreover, the body measuring system relating to the present invention, which is provided with the above-mentioned body measuring device, a user terminal through which data representing a physical change amount measured by the measuring sensor is acquired from the body measuring device, and a managing server provided with a database for managing the size and shape of an article to be attached to the body, is characterized in that when data representing the physical change amount is acquired from the body measuring device, the user terminal transmits the data representing the physical change amount thus acquired to the managing server so that upon receipt of the data representing the physical change amount from the user terminal, the managing server refers to the database and retrieves an article that is coincident with the data representing the physical change amount thus received, and transmits the results of retrieval to the user terminal.

Moreover, the body measuring system relating to the present invention, which is provided with the above-mentioned body measuring device, a user terminal through which data representing a physical change amount measured by the measuring sensor is acquired from the body measuring device, and a managing server provided with a database for managing the size and shape of a footwear, is characterized in that when data representing the physical change amount is acquired from the body measuring device, the user terminal transmits the data representing the physical change amount thus acquired to the managing server so that upon receipt of the data representing the physical change amount from the user terminal, the managing server refers to the database and retrieves a footwear that is coincident with the data representing the physical change amount thus received, and transmits the results of retrieval to the user terminal.

Additionally, any combination among the above-mentioned constituent elements and an arrangement in which the constituent elements and expressions of the present invention are included in the method, device, system, computer program, and recording media storing the computer program so as to be mutually substituted are also effectively used as modes of the present invention.

Effects of the Invention

The present invention relates to a body measuring device which, when attached to a user, specifies a size and shape of an attached body portion of the user, and is provided with a measuring sensor for measuring a physical change amount based upon a change in electrical characteristics, and the measuring sensor includes a pressure-type measuring sensor for measuring a pressure applied from the body of the user and an expansion-type measuring sensor for measuring a degree of expansion of a base member caused by the body shape of the user; therefore, even a user having no special size-taking technique is allowed to easily handle the device and can carry out the size-taking processes repeatedly.

BRIEF DESCRIPTION OF THE DRAWINGS

FIG. 4(a) and FIG. 4(b) are schematic cross-sectional views that explain a principle of a general pressure-type measuring sensor in accordance with the first embodiment of the present invention; FIG. 4(a) is a view showing a state where no pressure is applied thereto; and FIG. 4(b) is a view showing a state where a pressure is applied in a downward vertical direction.

FIG. 6(a) and FIG. 6(b) are schematic cross-sectional views showing one example of a configuration of a belt-shape expansion-type measuring sensor to be used for the body measuring device in the first embodiment of the present invention; FIG. 6(a) is a view showing a state where no expansion is exerted; and FIG. 6(b) is a view showing a state where an expansion is exerted in a plane direction.

FIG. 16 is a view showing one example of a data configuration of a user measurement DB in accordance with the first embodiment of the present invention.

FIG. 17 is a view showing one example of a data configuration of a footwear DB in accordance with the first embodiment of the present invention.

FIG. 21 is an exploded view showing one example of a configuration of a pressure-type measuring sensor for use in a body measuring device in accordance with a second embodiment of the present invention.

MODES FOR CARRYING OUT THE INVENTION

First Embodiment

[1] Outline of First Embodiment

A body measuring device 10 in accordance with the first embodiment of the present invention is designed such that when attached to a user, it measures the size and shape of the body portion of the user.

When a user terminal 20 acquires data such as the size or the like of the body from the body measuring device 10, it transmits the acquired data to a managing server 30.

Upon receipt of the data, the managing server 30 refers to the database installed therein, and retrieves any article that is coincident with the size and shape of the body of the user, for example, such as apparel commodities (clothes, footwear, hats, accessories or the like), and provides the results of retrieval to the user terminal 20.

The user browses the results of retrieval by using the user terminal 20, and can order any of the apparel commodities shown by the results of retrieval through the EC sites.

Figure 1:
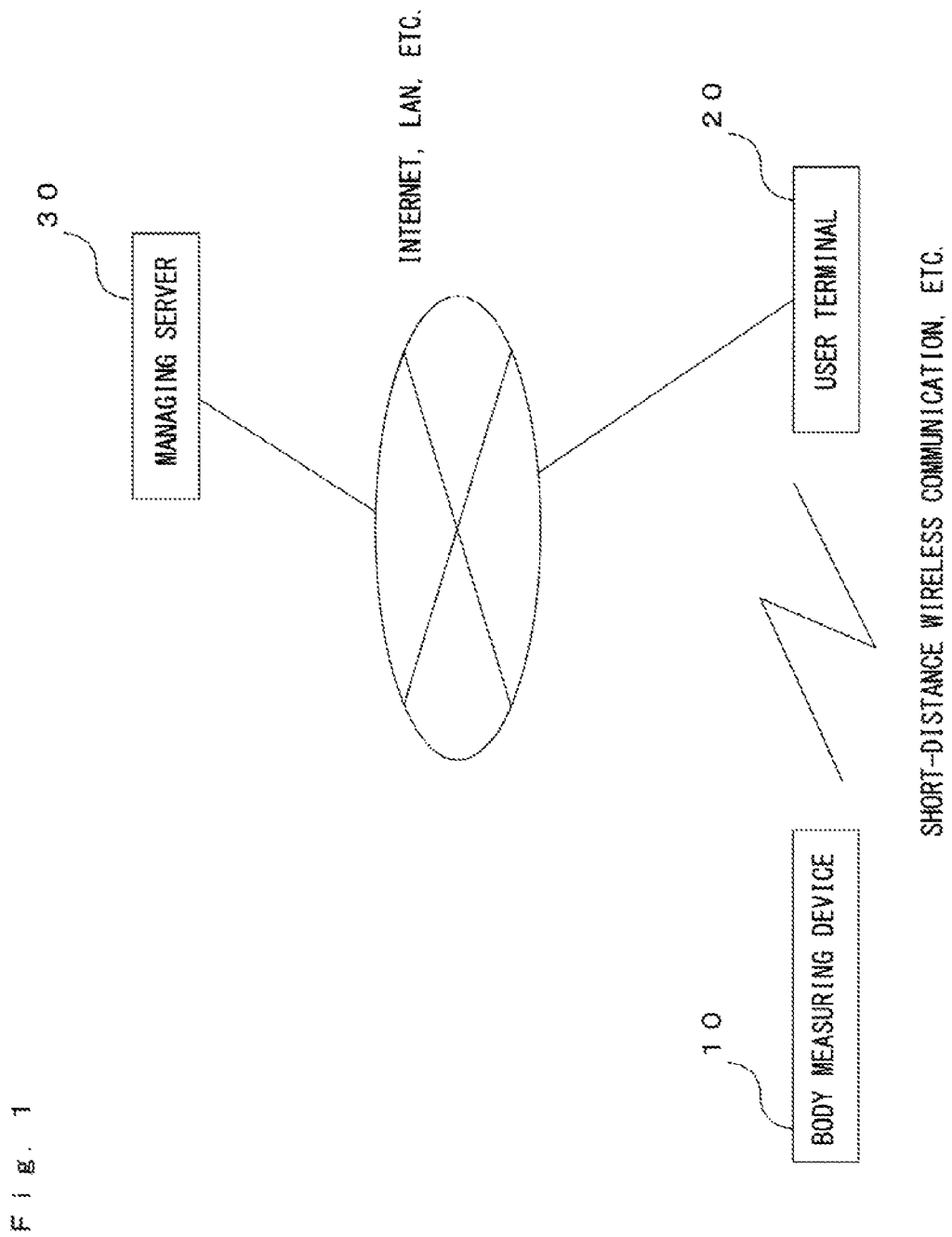
FIG. 1 is a view showing a configuration of a body measuring system in accordance with an embodiment of the present invention.

[2] Configuration of First Embodiment
(1) Entire Configuration of Body Measuring System FIG. 1 is a view showing the configuration of a body measuring system in accordance with embodiments of the present invention.

As shown in the drawing, the body measuring system is constituted by the body measuring device 10 that is attached to the body of the user so as to measure the size of the user's body, the user terminal 20 operated by the user who tries to measure the body and the managing server 30 that manages information, such as the size and shape of the user's body measured by the body measuring device 10, and information such as the size and shape of footwear or the like.

The body measuring device 10 and the user terminal 20 are communicatably connected with each other through a network, by using short-distance wireless communication, such as, for example, infrared rays, Wi-Fi, Bluetooth (registered trademark) or the like.

The user terminal 20 receives and acquires user measurement information including information of the size of the user's body measured by the body measuring device 10 from the body measuring device 10 through the network.

The managing server 30 and the user terminal 20 are communicatably connected with each other through a network, such as, for example, the Internet, LAN or the like.

The user terminal 20 transmits user measurement information acquired from the body measuring device 10 to the measuring server 30 through the network.

Upon receipt of the user measurement information from the user terminal 20, the managing server 30 stores the information in a database installed therein.

Moreover, the managing server 30 transmits information of footwear that is suitable for the size of the foot of the user to the user terminal 20.

The body measuring device 10 measures the size and shape of the body of the user although the portion of the body serving as its measuring object is not particularly limited, and in the present embodiment, the device is designed to have, for example, a shape of footwear, such as socks or the like, so as to measure the size and shape of the foot of the user, and the managing server 30 is designed to provide information of the footwear (shoes, socks or the like) suitable for the size and shape of the foot of the user.

(2) Configuration of Body Measuring Device 10

(Entire Configuration of Body Measuring Device 10)

The body measuring device 10 has a footwear shape, such as socks or the like, and is made of a material, such as freely expandable fibers or the like, as a whole. When the user attaches the body measuring device 10 to a foot of his or her own as if to put a footwear on his or her foot, the body measuring device 10 expands in response to the size and shape of the user's foot so as to measure the size and shape of the foot.

When the user removes the body measuring device 10 off as if to take the footwear off, the body measuring device 10 is returned to its original size and shape.

Figure 2:
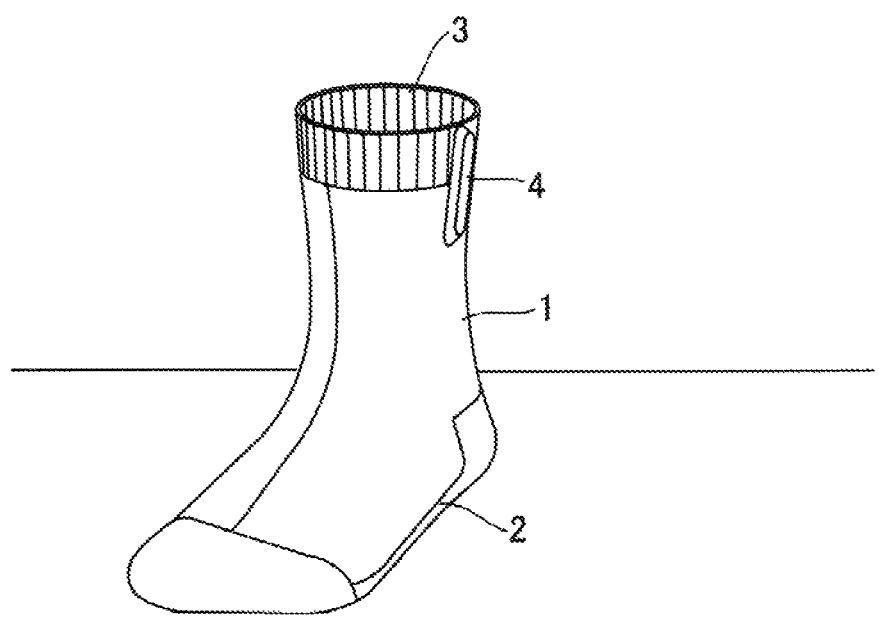
FIG. 2 is an external structural view showing a body measuring device in accordance with a first embodiment of the present invention.

FIG. 2 is an external structural view showing the body measuring device 10 in accordance with the first embodiment of the present invention. As shown in the drawing, the body measuring device 10 is constituted by a main body part 1 made of an expandable material and forming a main body portion except for the foot bottom portion of a footwear, a foot bottom part 2 made of an expandable material and forming the foot bottom portion of the footwear, an insertion opening part 3 made of an expandable material and forming an opening serving as an insertion opening of the footwear, and a measurement processing part 4 that executes processing or the like of measured values of the size and shape of the user's foot.

As expandable materials for the above-mentioned main body part 1, foot bottom part 2 and insertion opening part 3, for example, synthetic fibers or the like, which are formed by mixedly fabricating, for example, a spandex (polyurethane elastic fibers) with another non-expandable material, such as polyester, cotton or the like, are used, and any material for use in general clothes or the like may be used as long as it ensures its expandability and elasticity.

Figure 3:
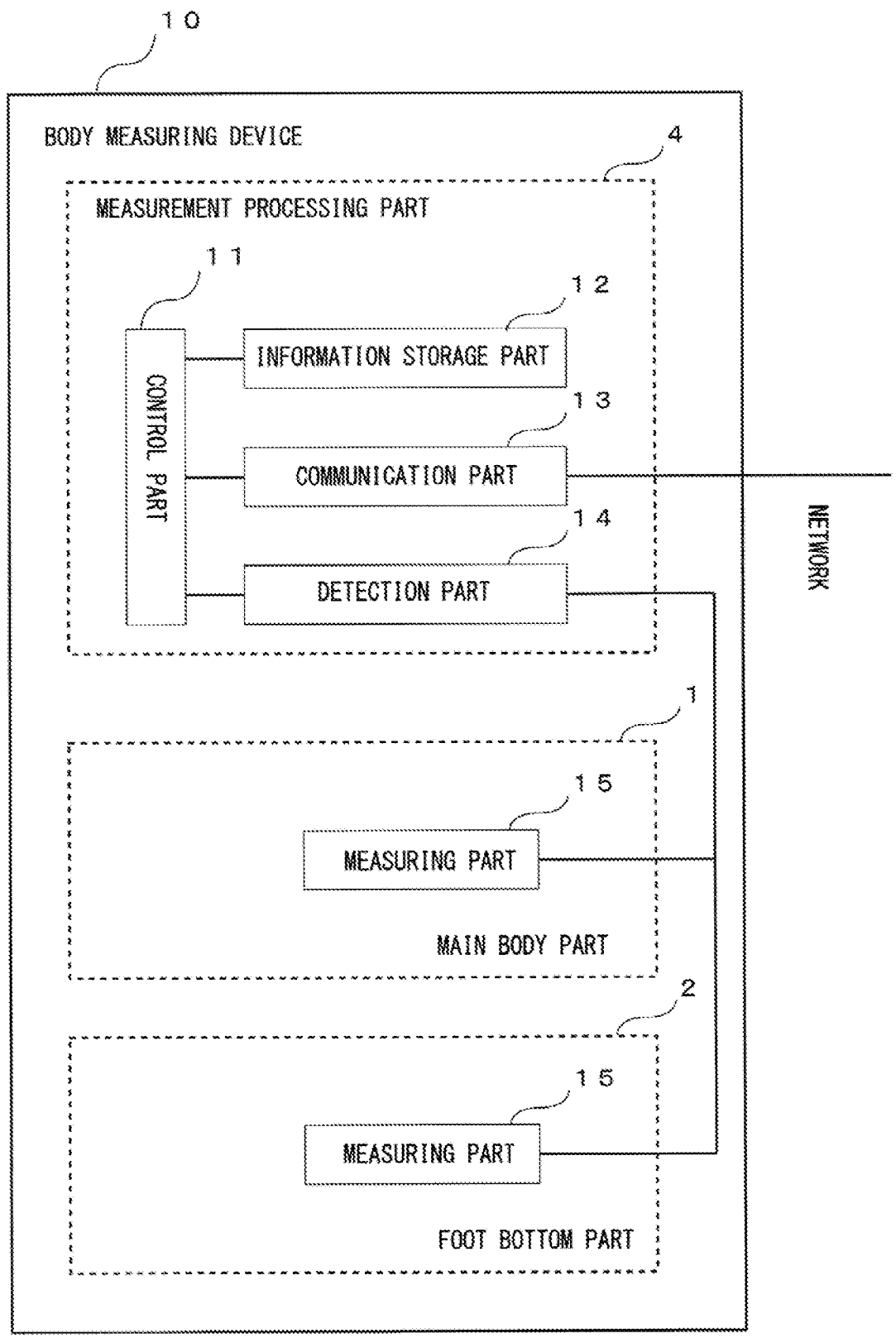
FIG. 3 is a block diagram showing the body measuring device in accordance with the first embodiment of the present invention.

FIG. 3 is a block diagram showing the body measuring device 10 in accordance with the first embodiment of the present invention.

As shown in the drawing, the measurement processing part 4 of the body measuring device 10 is provided with a control part 11 constituted by a CPU or the like for controlling the entire body measuring device 10, an information storage part 12 constituted by a ROM, a RAM or the like for storing user measurement information or the like, a communication part 13 for executing communication with the user terminal 20 by using short-distance wireless communication or the like, a detection part 14 for detecting a measured value of a measuring sensor to be described later, and a measuring part 15 constituted by one or more measuring sensors for measuring the size, shape or the like of the user's body.

The detection part 14 converts an analog signal indicating the size, shape or the like of the user's body measured by the measuring part 15 (measuring sensor) into a digital signal, and inputs the resulting signal to the control part 11.

The measuring part 15, which is constituted by a measuring sensor and allows the measuring sensor to measure a physical change amount based upon a change in electrical characteristics, is installed on the main body part 1 and the foot bottom part 2.

The measuring sensors include a pressure-type one and an expansion-type one, and these are used differently depending on portions of the body to be measured.

The following description will explain the configurations of the pressure-type and expansion-type measuring sensors respectively in detail.

(Pressure-Type Measuring Sensor)

FIG. 4(a) and FIG. 4(b) are schematic cross-sectional views that explain a principle of a general pressure-type measuring sensor in accordance with the first embodiment of the present invention; FIG. 4(a) is a view showing a state where no pressure is applied thereto; and FIG. 4(b) is a view showing a state where a pressure is applied thereto in a downward vertical direction.

Prior to the explanation of the configuration of a pressure-type measuring sensor 1100 to be used in the body measuring device 10 in accordance with the present embodiment by using the views, the configuration of a general pressure-type measuring sensor 1000 will be explained.

As shown in the drawings, the measuring sensor 1000 is constituted by a dielectric film 1001, and electrodes 1002 and 1003 that are respectively fixed onto the surface and rear surface of the dielectric film 1001.

The dielectric film 1001 is formed into a sheet shape, and made to be elastically deformable.

As a material forming the dielectric film 1001, it is mainly made of elastomer, and examples of the elastomer include silicone rubber, acrylonitrile butadiene copolymer rubber, acrylic rubber, epichlorohydrin rubber, chlorosulfonated polyethylene, chlorinated polyethylene, urethane rubber and the like.

The electrodes 1002 and 1003 are also formed into a sheet shape in the same manner as in the dielectric film 1001, and made to be elastically deformable.

As a material forming the electrodes 1001 and 1002, these are mainly made of elastomer, and examples of the elastomer include silicone rubber, ethylene-propylene copolymer rubber, natural rubber, styrene-butadiene copolymer rubber, acrylonitrile butadiene copolymer rubber, acrylic rubber, epichlorohydrin rubber, chlorosulfonated polyethylene, chlorinated polyethylene, urethane rubber and the like.

The electrostatic capacitance C of the measuring sensor 1000 can be found by using the following formula.

$$C = \varepsilon \cdot S/d \qquad \text{formula (1)}$$

(C: electrostatic capacitance, ε: dielectric constant, S: area of electrode 1002 (electrode 1003), d: distance between electrodes 1002 and 1003)

As shown in FIG. 4(a) and FIG. 4(b), in the case when, for example, a force is applied onto the electrode 1002 on the surface side of the measuring sensor 1000 in a downward vertical direction, since the area S of each of the dielectric film 1001 and the electrodes 1002, 1003 is slightly expanded so that the film thickness of a portion where the force is applied of the dielectric film 1001 becomes smaller to subsequently cause the distance d between the electrodes 1002 and 1003 to become smaller.

Then, as shown by the above-mentioned formula (1), the electrostatic capacitance C between the electrodes 1002 and 1003 increases.

Based upon the change in the electrostatic capacitance C, a magnitude of a load in the downward vertical direction applied as described above can be detected.

Next, the following description will explain an example in which the above-mentioned general pressure-type measuring sensor 1000 is applied to the body measuring device 10 in accordance with the present embodiment.

Figure 5:
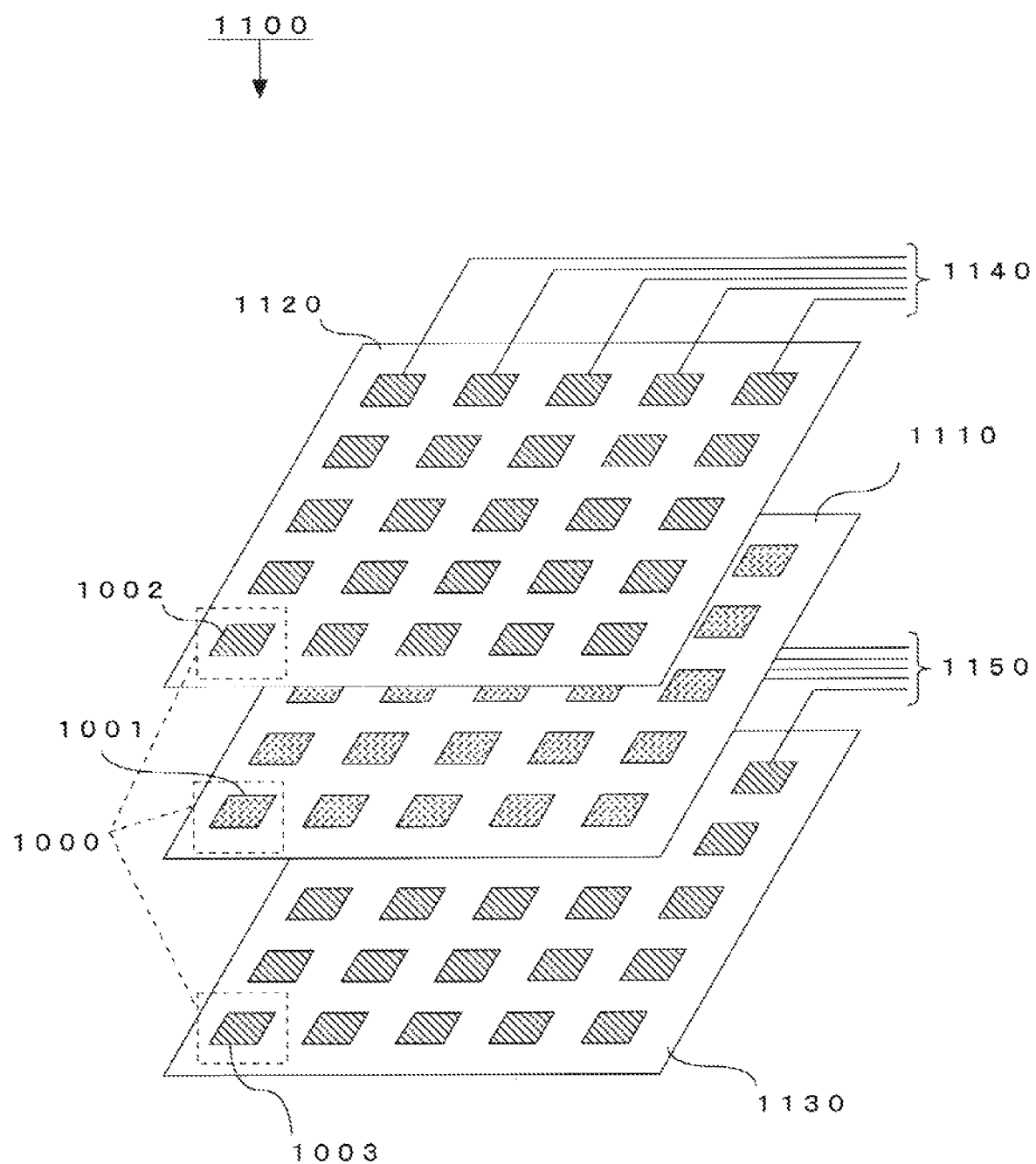
FIG. 5 is an exploded view showing one example of a configuration of a pressure-type measuring sensor to be used for the body measuring device in the first embodiment of the present invention.

FIG. 5 is an exploded view showing one example of the configuration of a pressure-type measuring sensor 1100 to be used for the body measuring device 10 in the first embodiment of the present invention.

The measuring sensor 1100 is constituted by installing a plurality of the above-mentioned pressure-type measuring sensors 1000. In the example shown in FIG. 5, in the pressure-type measuring sensor 1100, the total number of 25 pieces, that is, 5 pieces on each of 5 rows in the longitudinal and lateral directions, of the pressure-type measuring sensors 1000 are arranged on the same plane in a lattice pattern.

As shown in the drawing, the measuring sensor 1100 is constituted by the dielectric film substrate 1110 and a pair of electrode substrates 1120 and 1130 that are opposed to each other.

Additionally, in this drawing, for convenience of explanation, the dielectric film substrate 1110 and the electrode substrates 1120 and 1130 are illustrated in a separated manner; however, actually, in each of the measuring sensors 1000, the respective electrode substrates 1120 and 1130 are fixed onto both of the surface and rear surface of the dielectric film substrate 1110 so as to make respective electrodes 1002 and 1003 coupled to both of the surface and rear surface of the dielectric film substrate 1110.

On the electrode substrate 1120, the total number of 25 pieces, that is, 5 pieces on each of 5 rows in the longitudinal and lateral directions, of the electrodes 1002 are arranged in a lattice pattern, and the electrodes 1002 are directly attached to the respective dielectric films 1001 of the dielectric film substrate 1110 in one-to-one relation.

Moreover, in the same manner, on the electrode substrate 1130 also, the total number of 25 pieces, that is, 5 pieces on each of 5 rows in the longitudinal and lateral directions, of the electrodes 1002 are arranged in a lattice pattern, and the electrodes 1003 are directly attached to the respective dielectric films 1001 of the dielectric film substrate 1110 in one-to-one relation.

In this manner, since the respective electrodes 1002 and 1003 are attached to both of the surface and rear surface of each of the dielectric films 1001 in one-to-one relation, the measuring sensor 1100 is provided with a plurality of the independent sensors 1000.

To each of the electrodes 1002 of the electrode substrate 1120, one end of each of wires 1140 is individually connected, and the other end of each of the wires 1140 is connected to a detection part 14.

To each of the electrodes 1003 of the electrode substrate 1130, one end of each of wires 1150 is individually connected, and the other end of each of the wires 1150 is connected to the detection part 14.

In this manner, the electrodes 1002 and 1003 in each of the measuring sensors 1000 are connected to the detection part 14 through the wires 1140 and 1150 independently from the other measuring sensors 1000.

Additionally, in FIG. 5, the wires 1140 and 1150 connected to the other electrodes 1002 and 1003 except for the electrodes 1002 and 1003 on the uppermost row of the lateral 5 rows are omitted; however, the wires 1140 and 1150 are supposed to be connected to these electrodes in the same manner as in the electrodes 1002 and 1003 on the uppermost row.

As described above, in the measuring sensor 1100, the plural pressure-type measuring sensors 1000 are arranged on the same plane so that the detection part 14 detects the electrostatic capacitance of each of the measuring sensors 1000.

When, upon detecting the electrostatic capacitance of each of the measuring sensors 1000, a measuring signal forming a sine-wave waveform whose voltage is periodically varied is inputted between the electrodes 1002 and 1003 on both of the surface and rear surface sides, the detection part 14, which is provided with a power-supply circuit, forms a detection signal obtained by current-voltage converting the current that has passed through the measuring sensor 1000 as its output into a sine-wave waveform having the same frequency as that of the measuring signal.

The value of the detection signal obtained by the detection part 14 is stored in the information storage part 12.

Since this detection signal has its amplitude of the waveform varied in accordance with the electrostatic capacitance of the measuring sensor 1000, the electrostatic capacitance between the electrodes 1002 and 1003 can be measured (calculated) by measuring the amplitude.

Thus, it becomes possible to allow the detection part 14 to detect how much pressure is applied to the disposing position of which measuring sensor 1000 among the measuring sensors 1100.

Additionally, the measuring sensor 1100 shown in FIG. 5 is merely one example, and for example, the numbers, the intervals, the sizes, the shapes, the arrangement patterns or the like of the electrodes and dielectric films are not particularly limited.

(Expansion-Type Measuring Sensor)

As described above, the pressure-type measuring sensor 1100 is designed such that upon application of a pressure onto the electrode surface in a substantially vertical direction, its electrostatic capacitance is changed and by measuring the change amount, the pressure applied to the measuring sensor 1100 can be measured.

Moreover, since the measuring sensor using the above-mentioned electrode and dielectric film also has its electrostatic capacitance varied when expanded in a plane direction, it may also be used as the expansion-type measuring sensor that measures how much degree the measuring sensor is physically expanded by measuring the change amount of the electrostatic capacitance.

The following description will explain the configuration of an expansion-type measuring sensor 1200 installed in the body measuring device 10.

FIG. 6(*a*) and FIG. 6(*b*) are schematic cross-sectional views showing one example of a configuration of a belt-shape expansion-type measuring sensor 1200 to be used for the body measuring device 10 in the first embodiment of the present invention; FIG. 6(*a*) is a view showing a state where no expansion is exerted; and FIG. 6(*b*) is a view showing a state where an expansion is exerted in a plane direction.

As shown in FIG. 6(*a*) and FIG. 6(*b*), for example, when a force is applied to electrodes 1202 and 1203 of the measuring sensor 1200 in an expanding direction relative to the plane direction thereof, the area S of a dielectric film 1201 and the electrodes 1202 and 1203 is expanded to make the film thickness of the dielectric film 1201 smaller, with the result that the distance d between the electrodes 1202 and 1203 becomes smaller. With this change, in accordance with the above-mentioned formula (1), the electrostatic capacitance C between the electrodes 1202 and 1203 increases.

In the present embodiment, the above-mentioned belt-shape expansion-type measuring sensor 1200 is installed on the main body part 1 and the foot bottom part 2 so as to be expanded substantially linearly in the belt length direction, when the body measuring device 10 is attached to the user.

To the respective electrodes 1202 and 1203, one end of each of wires is connected, and the other end of the wire is connected to the detection part 14.

In the same manner as in the case of the pressure-type measuring sensor 1100, when a detection signal from the measuring sensor 1200 is inputted thereto, the detection part 14 stores the value of the detection signal in the information storage part 12.

Since the detection signal has its amplitude of the waveform varied in response to the electrostatic capacitance between the electrodes 1202 and 1203, the electrostatic capacitance between the two electrodes 1202 and 1203 can be measured (calculated) by measuring the amplitude.

(Attaching Example of Measuring Sensor)

Onto the foot bottom part 2 of the body measuring device 10, the above-mentioned pressure-type measuring sensor 1100 and expansion-type measuring sensor 1200 are installed.

Figure 7:
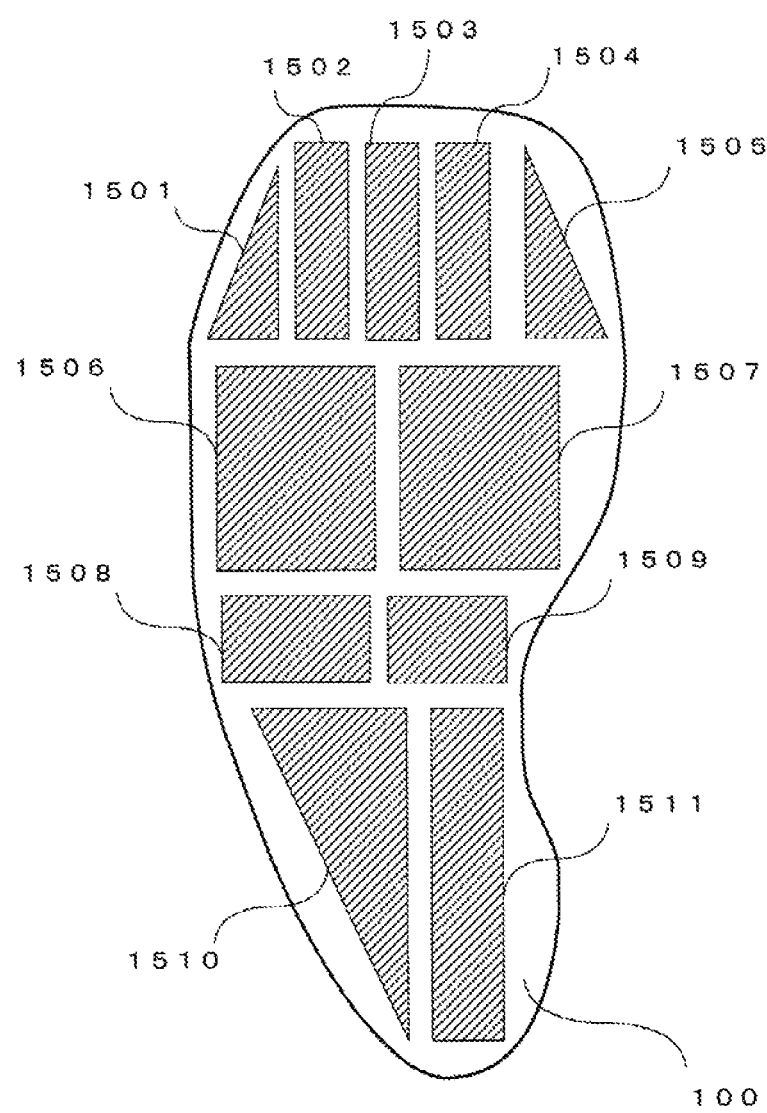
FIG. 7 is a view showing one example of attached positions of measuring sensors on a bottom portion of a left foot of a body measuring device having a footwear shape in accordance with the first embodiment of the present invention.

FIG. 7 is a view showing one example of attached positions of measuring sensors on the foot bottom part 2 for a left foot of the body measuring device 10 in accordance with the first embodiment of the present invention.

Referring to the drawing, the following description will explain the layout and actuated operation of the measuring sensor of the foot bottom part 2 of the body measuring device 10.

In an example shown in the drawing, measuring sensors 1501 to 1511 are disposed on the foot bottom part 2 of the body measuring device 10, and among these, the measuring sensors 1501 to 1505 are expansion-type measuring sensors 1200, and the measuring sensors 1506 to 1511 are pressure-type measuring sensors 1100.

Additionally, although not illustrated in the drawing, the respective measuring sensors 1501 to 1511 are connected to the detection part 14 through wires, and the control part 11 calculates the value of the electrostatic capacitance of each of the measuring sensors 1501 to 1511 by using the same method as the above-mentioned method.

(Measuring Sensors 1501 to 1505)

The measuring sensors 1501 to 1505 are disposed so as to correspond to the positions of respective toes on the toe side of the foot bottom. In an example shown in the drawing, the measuring sensors 1501 to 1505 correspond to the positions of the big toe, second toe, third toe, fourth toe and little toe.

The lengths of the toes of humans are different for each individual person, and for example, there are various types of the shape of a foot, such as a Roman type in which the big toe, the second toe and the third toe have substantially the same length, a Greek type in which the second toe is the longest, or the like.

Since the measuring sensors 1501 to 1505 measure the foot length (length from the toe to the heel) of a user, as well as the lengths of the respective toes of the user's foot, individually, a footwear that fits to the shape of the corresponding foot can be provided, whatever type of the shape the user's foot belongs to.

The respective sensors 1501 to 1505 and the base member 100 in the body measuring device 10 are made of expandable materials; therefore, when the user attaches the body measuring device 10 to his or her own foot as if to put socks on, the measuring sensors 1501 to 1505 expand in the toe direction (in the belt length direction of the belt-shaped measuring sensors) together with the toe side base member 100 in accordance with the lengths of the respective toes of the user, while the toe tips are made in touch with the inside of each of the toe portions of the main body part 1 of the body measuring device 10; thus, the area S of the electrodes is expanded so that the distance d between the electrodes becomes smaller, with the result that the electrostatic capacitance increases.

The control part 11 calculates the value of the electrostatic capacitance in each of the measuring sensors 1501 to 1505 or the change amount (amount of increase) thereof by using the same method as in the case of the expansion-type measuring sensor 1200 as described above.

The body measuring device 10 transmits information indicating the calculated value of the electrostatic capacitance of each of the measuring sensors 1501 to 1505 to the user terminal 20.

Based upon the value of the electrostatic capacitance of each of the measuring sensors 1501 to 1511 received from the body measuring device 10, the user terminal 20 specifies the lengths of the respective toes and the shapes of the toes of the user's foot.

(Measuring Sensors 1506 to 1511)

The measuring sensors 1506 to 1511 are disposed so as to cover the entire foot bottom from the center portion toward the heel side of the foot bottom. In an example shown in the drawing, the measuring sensors 1506 and 1507 are disposed so as to correspond to the center portion of the foot bottom, the measuring sensors 1508, 1509 are disposed so as to correspond to the arch portion (foot arch) of the foot bottom, and the measuring sensors 1510 and 1511 are disposed so as to correspond to the heel portion of the foot bottom.

The control part 11 calculates the electrostatic capacitance or the electrostatic capacitance changed by a pressure from the sole of the user of each of the measuring sensors 1506 to 1511 by using the same method as in the case of the pressure-type measuring sensor 1100 as described above.

The body measuring device 10 transmits information indicating the calculated value of the electrostatic capacitance to the user terminal 20.

The user terminal 20 specifies the size and shape of the sole of the user based upon the value of the electrostatic capacitance of each of the measuring sensors 1506 to 1511 received from the body measuring device 10.

In the example of the present embodiment, the pressure from the sole of the user exerted by each of the plural measuring sensors 1506 to 1511 is measured; however, the pressure may be measured by using a single measuring sensor.

(Measuring Sensors 1521 to 1524)

In the body measuring device 10, annular expansion-type measuring sensors are installed along a circumferential (foot surrounding) direction in a cross section of a foot that is substantially orthogonal to a direction in a length (foot length) of a foot bottom (direction from the heel to the toe) in the main body part 1.

The corresponding annular expansion-type measuring sensor is formed into an annular shape by connecting the two ends in the belt length direction of the aforementioned belt-shaped expansion-type measuring sensor 1200.

Figure 8:
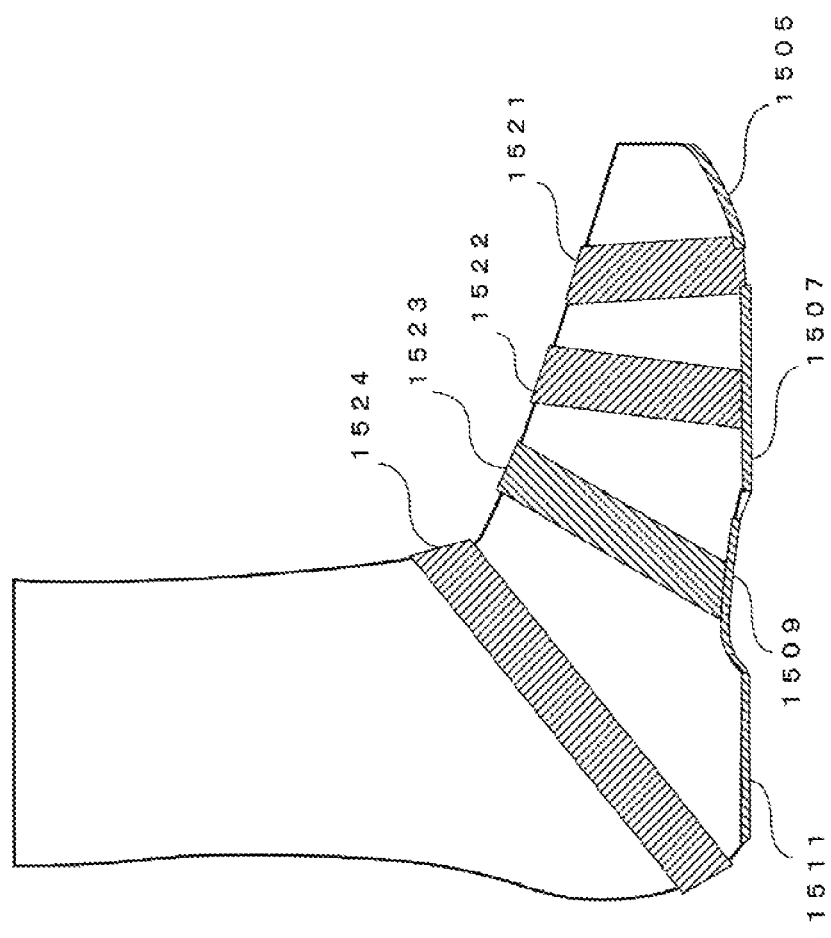
FIG. 8 is a side view showing one example of attached positions of measuring sensors in a foot surrounding direction of a main body part of the body measuring device in accordance with the first embodiment of the present invention.

FIG. 8 is a side view showing one example of attached positions of measuring sensors in a foot surrounding direction of the main body part 1 of the body measuring device 10 in accordance with the first embodiment of the present invention.

Figure 9:
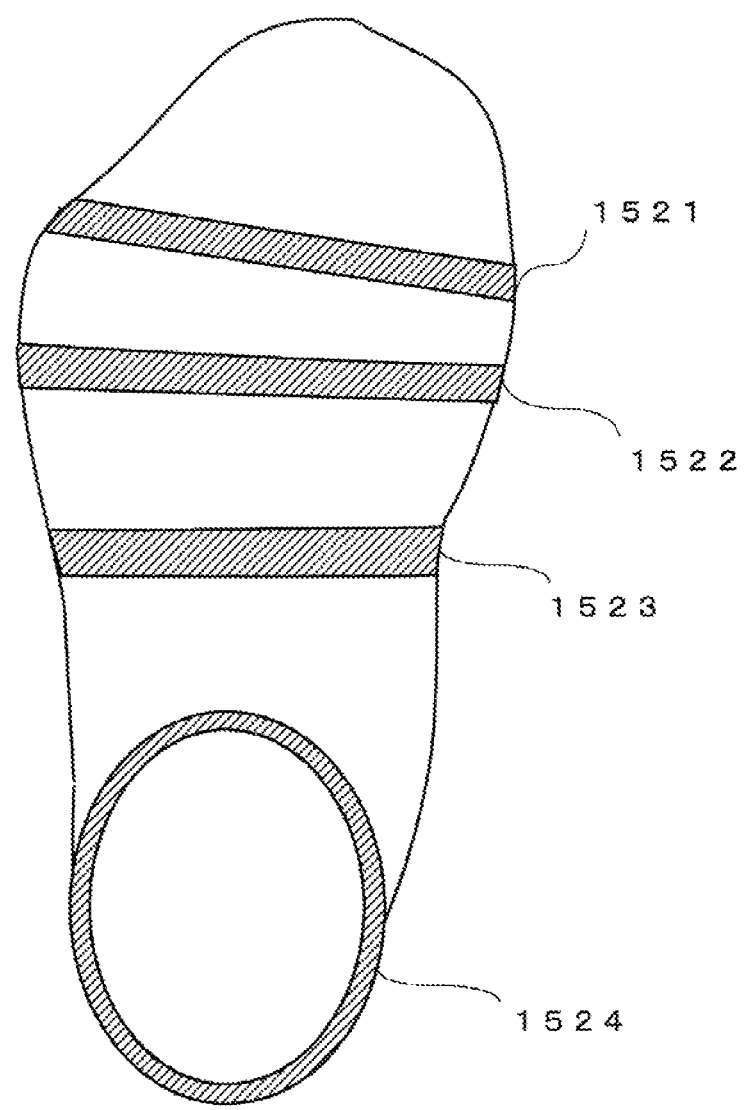
FIG. 9 is a plan view showing an example of attached positions of measuring sensors in a foot surrounding direction of a main body part of the body measuring device in accordance with the first embodiment of the present invention.

Moreover, FIG. 9 is a plan view showing an example of attached positions of measuring sensors in a foot surrounding direction of the main body part 1 of the body measuring device 10 in accordance with the first embodiment of the present invention.

As shown in the drawing, in a direction from the toe toward the heel, annular expansion-type measuring sensors 1521, 1522, 1523 and 1524 are respectively installed at positions of the ball, waist, instep and heel in a foot surrounding direction (circumferential direction).

Each of the annular measuring sensors 1521 to 1524 is designed so as to make its circumferential length shorter than the general size of the foot surrounding.

When a user puts on the socks-state body measuring device 10 so as to attach it to his or her own foot, the annular measuring sensors 1521 to 1524 disposed along the outer circumferential surface of the main body part 1 are expanded in accordance with the size and shape of the user's foot to make the value of electrostatic capacitance of each of the measuring sensors 1521 to 1524 varied.

The control part 11 calculates the value of electrostatic capacitance of each of the measuring sensors 1521 to 1524 by using the same method as the method described above.

The body measuring device 10 transmits information indicating the calculated value of the electrostatic capacitance to the user terminal 20.

Based upon the value of the electrostatic capacitance of each of the measuring sensors 1521 to 1524 received from the body measuring device 10, the user terminal 20 specifies the lengths in the circumferential direction of the respective positions of the ball, waist, instep and heel of the user's foot.

Figure 10:
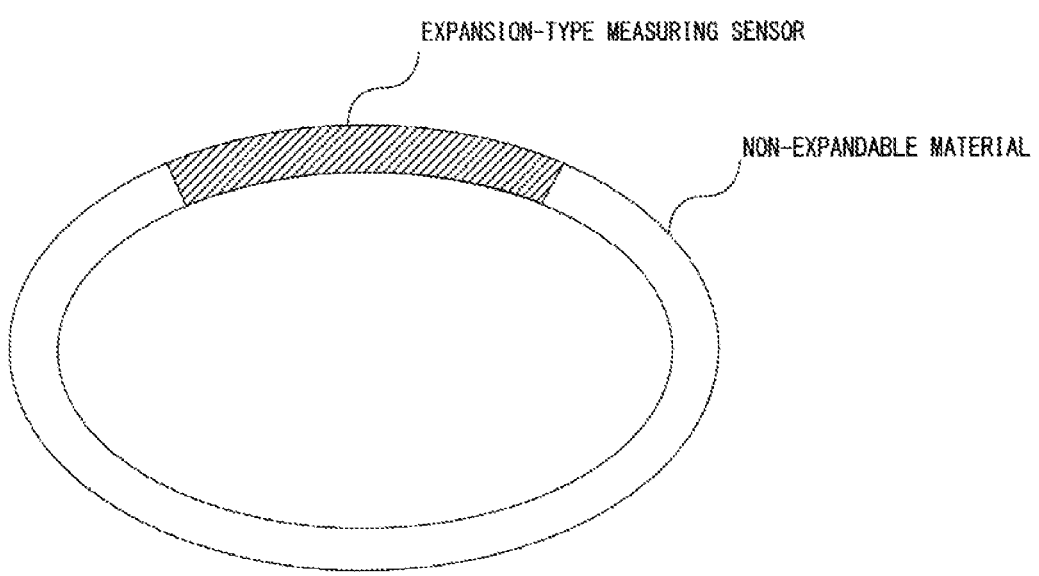
FIG. 10 is a view showing another example of an annular expansion-type measuring sensor in accordance with the first embodiment of the present invention.

FIG. 10 is a view showing another example of an annular expansion-type measuring sensor in accordance with the first embodiment of the present invention.

The above-mentioned annular expandable sensor has a structure in which expandable electrodes and dielectric films are installed along all circumference of the annular shape; however, in the measuring sensor of another example shown in FIG. 10, one portion of the annular shape is constituted by expandable electrodes and dielectric films, with the other portion being constituted by non-expandable materials.

The two ends of each of the expandable electrodes and dielectric films and the two ends of each of the non-expandable materials are connected with each other to be formed into annular shapes.

In the annular measuring sensor of the other example shown in FIG. 10, only one portion is expanded, and by the change in the value of the electrostatic capacitance caused by the expansion, the entire length of the measuring sensor is detected by the control part 11.

In this manner, by forming only the one portion of the annular measuring sensor by using expandable electrodes and dielectric films, with the other portion being formed by using inexpensive non-expandable materials (cloth material, fibers), the manufacturing costs of the measuring sensors can be greatly reduced.

Moreover, by forming one portion of the measuring sensor by using a non-expandable material, the strength of the main body part 1 of the body measuring device 10 can be maintained at a predetermined level or more so that it is possible to prevent the occurrence of a deformation or the like.

(3) Configuration of User Terminal 20

The user terminal 20, which is an information processing device operated by a user so as to measure the size and shape of the body of himself or herself, is prepared as, for example, a smartphone, a tablet-type terminal, a portable telephone, a PDA, a PC or the like.

Figure 11:
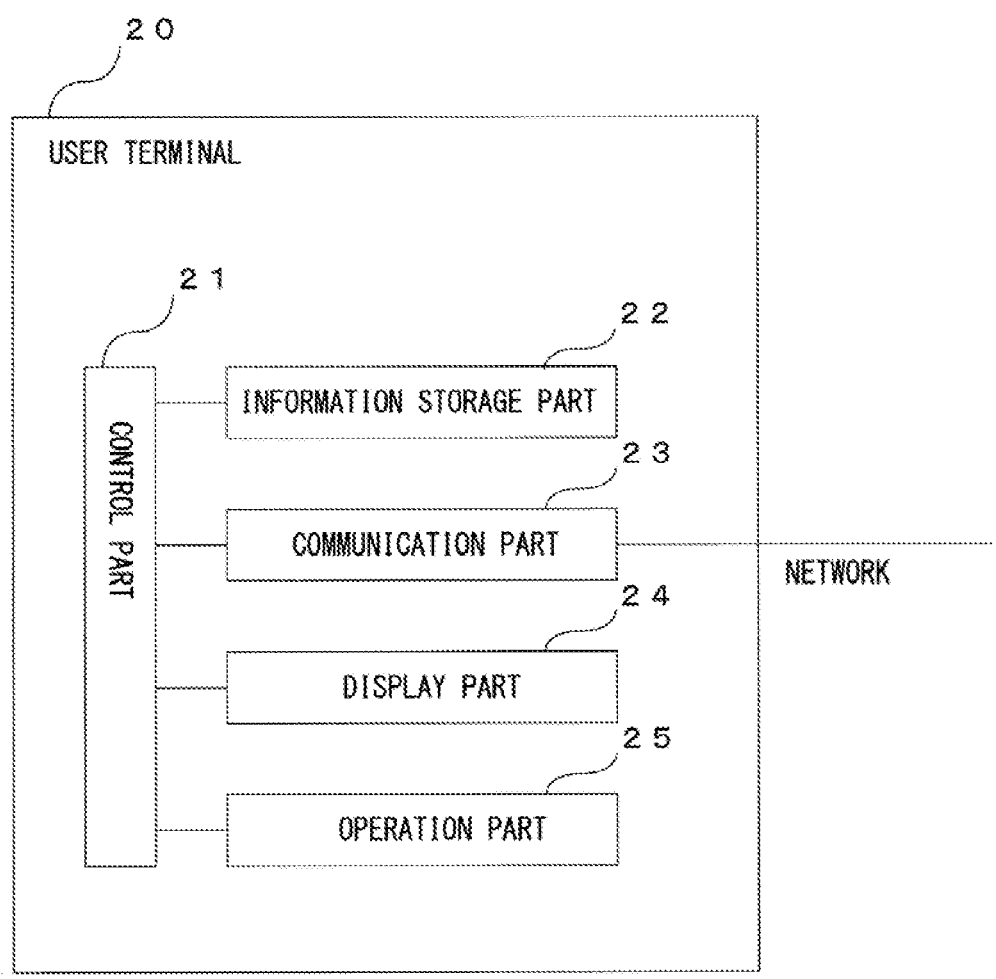
FIG. 11 is a block diagram showing a configuration of a user terminal in accordance with the first embodiment of the present invention.

FIG. 11 is a block diagram showing the configuration of the user terminal 20 in accordance with the first embodiment of the present invention.

As shown in the drawing, the user terminal 20 is constituted by a control part 21 for controlling the entire user terminal 20, which is constituted by a CPU or the like, an information storage part 22 for storing various types of information, a communication part 23 that carries out communications with a managing server 30 through a network, such as the Internet, LAN or the like, and also carries out communications with the body measuring device 10 through a short-distance wireless communication, such as wireless LAN, Bluetooth (registered trademark) or the like, a display part 24 for displaying information on a display or the like and an operation part 25 for carrying out inputs of information through various types of keys, a touch panel, a microphone or the like.

Additionally, as described above, the user terminal 20 desirably transmits or receives information to or from the body measuring device 10 by the short-distance wireless communication; however, the communications may be carried out through wires (cables) coupled with one another.

In the information storage part 22, various kinds of data of the respective measuring sensors 1501 to 1511 and 1521 to 1524 are stored.

With respect to the pressure-type measuring sensors 1506 to 1511, the information storage part 22 stores data indicating correspondence between the electrostatic capacitance of the measuring sensor 1000 installed in each of the measuring sensors 1506 to 1511 and the numeric value of a pressure applied to the measuring sensor 1000, and data representing the positional information (coordinates) of each of the corresponding measuring sensors 1000.

Thus, upon receipt of information relating to the value of the electrostatic capacitance of each of the pressure-type measuring sensors 1000 from the body measuring device 10, the user terminal 20 recognizes that a pressure is being applied to the measuring sensor 1000 which has a change in the value of its electrostatic capacitance from the sole of the user so that the sole of the user is on the ground.

In contrast, with respect to the measuring sensor 1000 which has no change in the value of its electrostatic capacitance, the control part 21 of the user terminal 20 recognizes that no pressure is applied from the sole of the user, that is, the sole of the user is not on the ground at the position of the corresponding measuring sensor 1000.

In this manner, the user terminal 20 is designed to specify the shape of the sole.

Moreover, based upon the value of the electrostatic capacitance thus received, the user terminal 20 refers to the above-mentioned data, and can find out how much pressure is applied to which measuring sensor 1000. Thus, the user terminal 20 may carry out a process while, for example, ignoring the portion where a pressure of a predetermined value or less is applied as an error, and may find out a footwear that is correctly suitable for the sole of the user.

With respect to the expansion-type measuring sensors 1501 to 1505 and 1521 to 1524, the information storage part 22 stores data indicating correspondence between the electrostatic capacitance and the value of the length in the expanding direction of the measuring sensor 1200, and data representing the positional information (coordinates) of each of the corresponding measuring sensors 1501 to 1505 and 1521 to 1524.

Thus, upon receipt of information relating to the value of the electrostatic capacitance of each of the expansion-type measuring sensors from the body measuring device 10, the user terminal 20 uses the data indicating correspondence between the above-mentioned electrostatic capacitance and the length of the measuring sensor and the data of positional information, and based upon the change amount of the electrostatic capacitance caused by the expansion in the corresponding belt direction by the body measuring device 10, detects how much length the measuring sensor has been expanded from which reference position physically determined preliminarily, and specifies the length of the toe of the user's foot, the shape of the toe and the length of the circumference of the foot based upon the degree of its expansion.

As described above, when the user terminal 20 has received information indicating the value of the electrostatic capacitance of each of the measuring sensors 1501 to 1511 from the body measuring device 10 through a short-distance wireless communication or the like, the control part 21 of the user terminal 20 specifies the size and shape of the user's foot based upon the change amount of the electrostatic capacitance.

Moreover, based upon the size and shape of the foot thus specified, the control part 21 generates a grounding map corresponding to image information showing a grounding state of the sole of the user, and displays the map on a display part 24.

Figure 12:
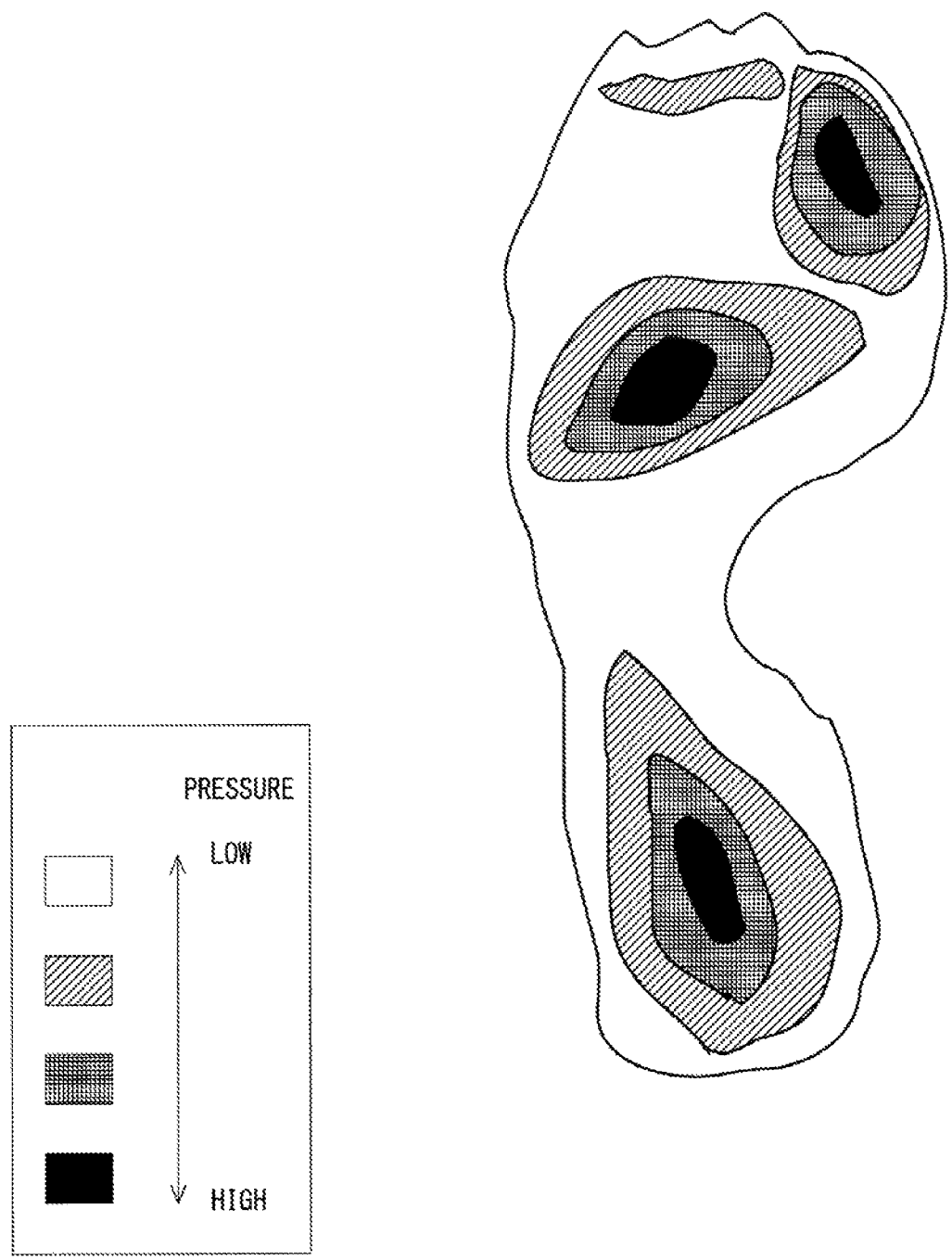
FIG. 12 is a view showing one example of a grounding map of the sole in accordance with the first embodiment of the present invention.

FIG. 12 is a view showing one example of the grounding map of the sole in accordance with the first embodiment of the present invention.

The present grounding map is illustrated in the following manner based upon the value of the electrostatic capacitance measured by each of the expansion-type measuring sensors 1501 to 1505 and the pressure-type measuring sensors 1506 to 1511.

In the example shown in the drawing, as described above, of the sole of the user, with respect to the toe portion from the base of the toe to the toe tip, the length and shape of the toe are specified by the expansion of each of the measuring sensors 1501 to 1505, and illustrated on the grounding map.

Moreover, with respect to portions except for the toe portion of the sole of the user (arch portion, heel portion or the like), of the measuring sensors 1000 in the respective measuring sensors 1506 to 1511, the grounded portion of the sole of the user is illustrated like the isobaric line in accordance with the degree (degree of value of electrostatic capacitance) of the pressure.

With respect to the region of the sole where no measuring sensor 1000 is placed, the control part 21 of the user terminal 20 carries out a compensating process, for example, based upon the electrostatic capacitance of one or more measuring sensors 1000 located on the periphery thereof. As the compensating method, for example, based upon the average value of the electrostatic capacitance of one or more measuring sensors 1000 located on the periphery thereof, the portion may be illustrated like the isobaric line, or the compensating process may be carried out by using other conventionally known methods.

The user can easily confirm the shape of the foot of his or her own by viewing the grounding map of the sole of himself or herself displayed on the display part 24.

Moreover, when the user specifies any two points on the grounding map by using the operation part 25, the control part 21 measures the length between the corresponding two points based upon the positional information data of the measuring sensors, and displays the length on the display part 24.

Moreover, the control part 21 of the user terminal 20 calculates respective sizes (for example, respective lengths fd1 to fd4 to be described later) of the sole based upon the pressure distribution on the sole based upon the grounding map, and can display the results of the calculations on the display part 24.

Figure 13:
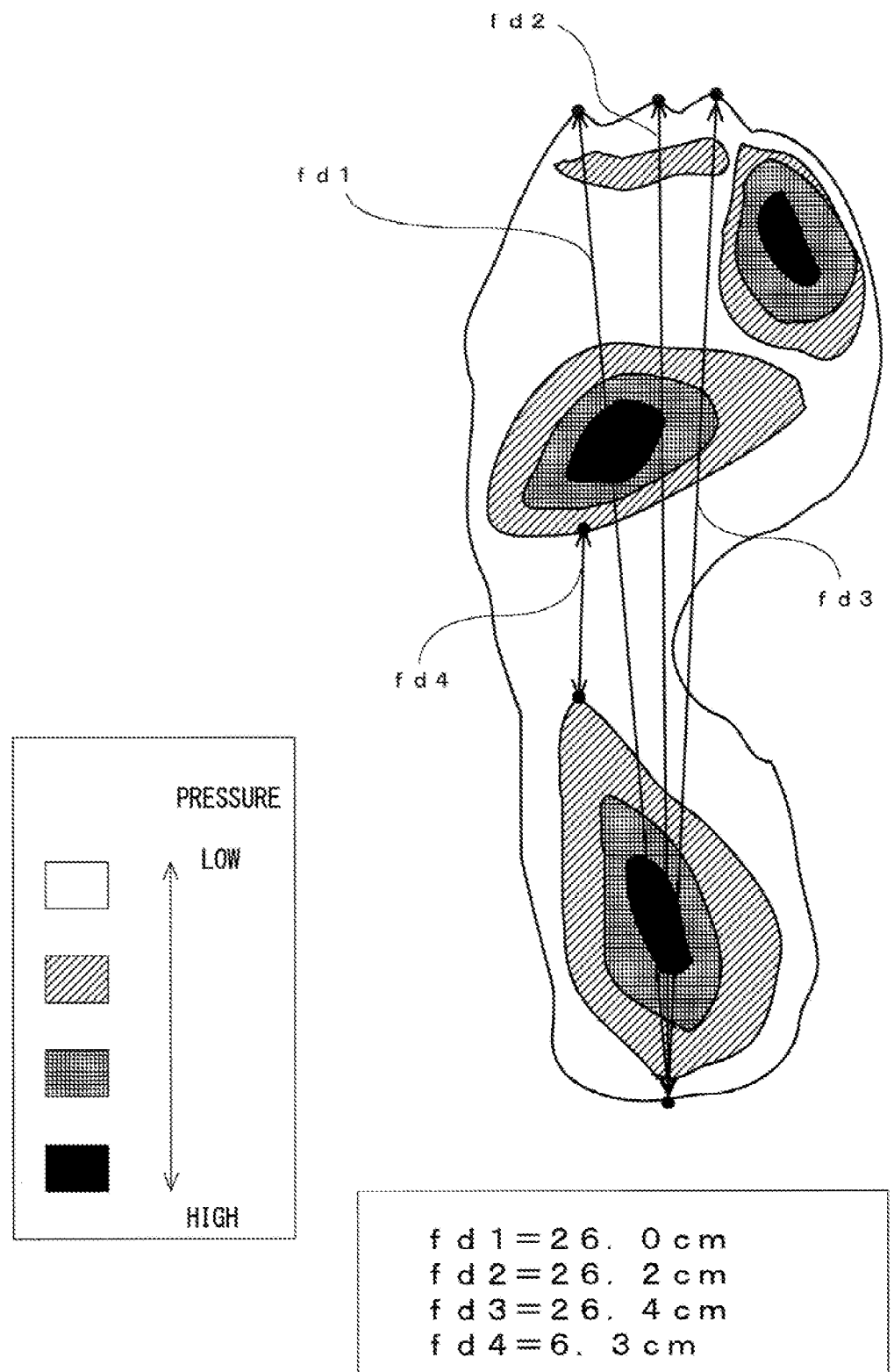
FIG. 13 is a view showing a state in which the size of the sole is detected based upon the grounding map of the sole in accordance with the first embodiment of the present invention.

FIG. 13 is a view showing a state in which the size of the sole is detected based upon the grounding map in accordance with the first embodiment of the present invention.

In the example of FIG. 13, the length from the heel to the tip of the fourth toe (=fd1), the length from the heel to the tip of the third toe (=fd2), the length from the heel to the second toe (=fd3) and the length of the arch (arch portion) (=fd4) are respectively detected and shown.

By detecting the lengths fd1 to fd3 from the heel to the respective tips of toes, a footwear suitable for the shape of a foot depending on various lengths of toes, such as a Roman type or the like, can be easily found out.

Moreover, by detecting the length fd4 of the arch, a footwear suitable for the shape of a foot can be easily found out so that a shoe sore or the like can be prevented.

Figure 14:
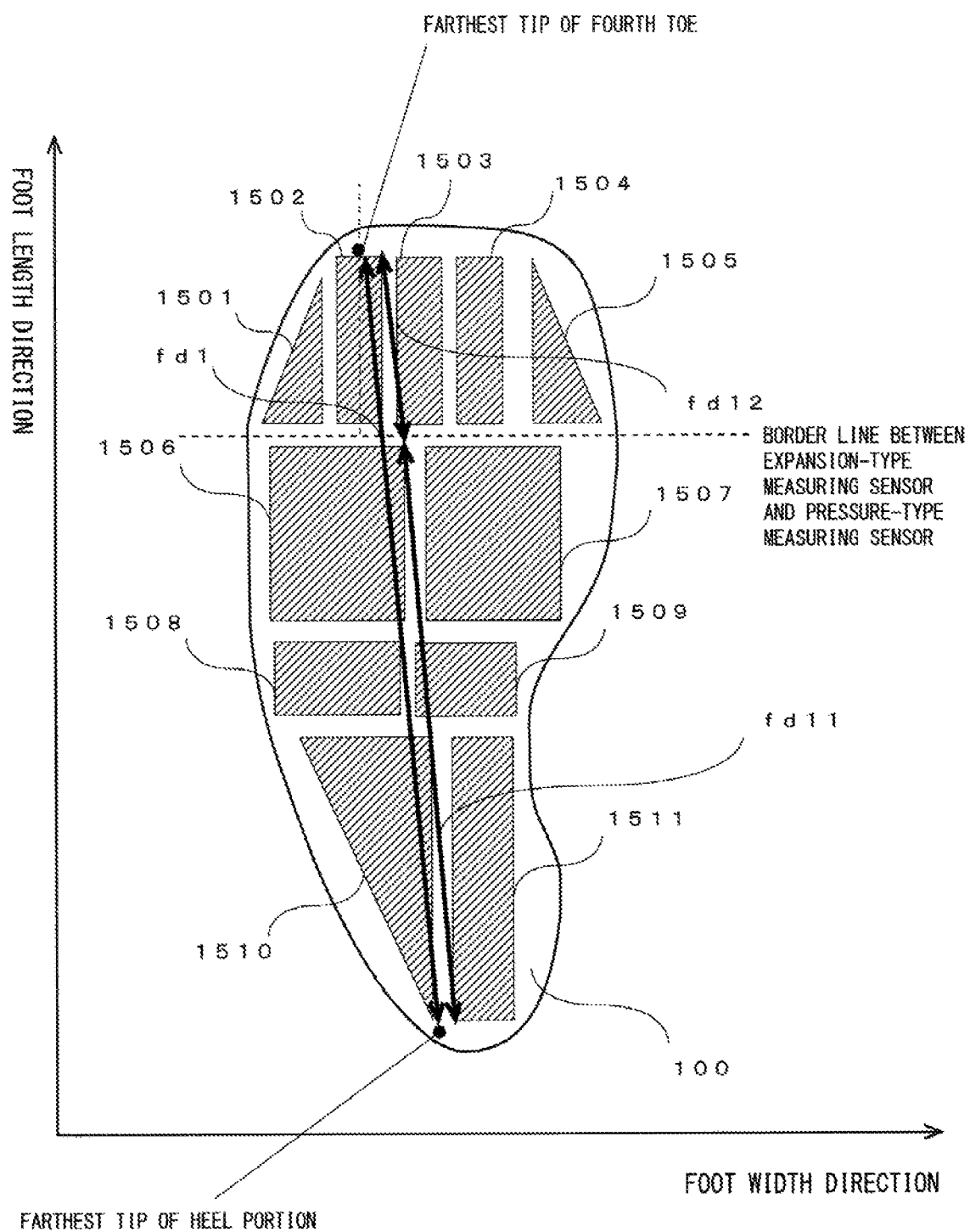
FIG. 14 is a view showing one example of a calculation method of a length from a heel to a tip of a fourth toe in accordance with the first embodiment of the present invention.

FIG. 14 is a view showing one example of the calculation method of the length fd1 from the heel to the tip of the fourth toe in accordance with the first embodiment of the present invention.

Referring to the drawing, the following description will explain the calculation method for the length fd1 from the heel to the tip of the fourth toe.

The position of the farthest tip of the heel portion of the user corresponds to coordinates at the farthest tip in a direction toward the heel of positions where pressures are detected in the measuring sensors 1510 and 1511.

The positional coordinates of the farthest end of the tip of the fourth toe can be found out in the following manner.

The coordinates in the foot length direction of the farthest end of the tip of the fourth toe can be found by adding the length of the expanded portion of the measuring sensor 1502 to the coordinates in the foot length direction on the border line between the expansion-type measuring sensors 1501 to 1505 and the pressure-type measuring sensors 1506 and 1507.

Moreover, as the coordinates of the farthest end of the tip of the fourth toe in the foot width direction, any point in the foot width direction of the measuring sensor 1502, that is, for example, the coordinates of the midpoint in the foot width direction of the measuring sensors 1502 forming a rectangular shape, is adopted.

The length of a line segment connecting the coordinates of farthest end of the heel portion and the coordinates of the farthest end of the tip of the fourth toe obtained as described above is calculated as the length fd1 from the heel to the tip of the fourth toe.

In the same manner as in the above-mentioned calculation method of the length fd1 from the heel to the tip of the fourth toe, the length fd2 from the heel to the tip of the third toe and the length fd3 from the heel to the tip of the second toe are calculated. In the case of the length fd2 from the heel to the tip of the third toe, the measuring sensor 1503 is used in place of the measuring sensor 1502, and in the case of the length fd3 from the heel to the tip of the second toe, the measuring sensor 1504 is used.

The length fd4 of the arch (arch portion) is found out in the following manner.

As described above, each of the pressure-type measuring sensors 1506 to 1511 measures a pressure received from the sole of the user.

As shown in the example of FIG. 13, pressures received from the foot ball portion and the heel portion respectively form isobaric lines (closed curve lines) indicating respectively predetermined pressure values.

Moreover, in FIG. 13, the distance between a point which is located on the closest side to the heel in the foot length direction on an isobaric line (closed curve line) indicated by slanting lines of the isobaric line (closed curve line) indicating a predetermined pressure value corresponding to the foot ball portion and a point which is located on the closest side to the toe in the foot length direction on an isobaric line (closed curve line) indicated by slanting lines of the isobaric line (closed curve line) indicating a predetermined pressure value corresponding to the heel portion is found out as the length fd4 of the arch (arch portion).

As described above, when the user terminal 20 has received information indicating the value of the electrostatic capacitance of each of the measuring sensors 1521 to 1524 from the body measuring device 10 through a short-distance wireless communication or the like, the control part 21 of the user terminal 20 detects lengths fd21, fd22, fd23 and fd24 after the expansion of the respective measuring sensors 1521, 1522, 1523 and 1524, that is, the lengths of the outer circumferences of the respective portions of the user's foot, based upon the change amount of the electrostatic capacitance.

As described above, since the measuring sensors 1521 to 1524 measure the respective outer circumferences of cross sections that are substantially orthogonal to the length direction of the user's foot, it becomes possible to easily find out a footwear suitable for the size and shape of the user's foot.

In particular, by combining the measured value of the measuring sensor 1523 for measuring the outer circumference of the instep portion of the foot with the above-mentioned measured value of each of the measuring sensors 1508 and 1509 for measuring the arch portion (foot arch portion) of the bottom of the foot, the size and shape of the arch portion of the user's foot are detected in detail so that it becomes possible to easily find out a footwear suitable for the size and shape of the arch and consequently to prevent the occurrence of a shoe sore.

(4) Configuration of Managing Server

The managing server 30 registers user measurement information transmitted from the user terminal 20 so as to manage the information, and preliminarily stores footwear information indicating the sizes or the like of a plurality of types of footwear, such as shoes or the like, so that it serves as an information processing device, which based upon the user measurement information that has been received, refers to the footwear information, and retrieves a footwear suitable for the size and shape of the user's foot so as to provide the results of the retrieval to the user terminal 20.

Figure 15:
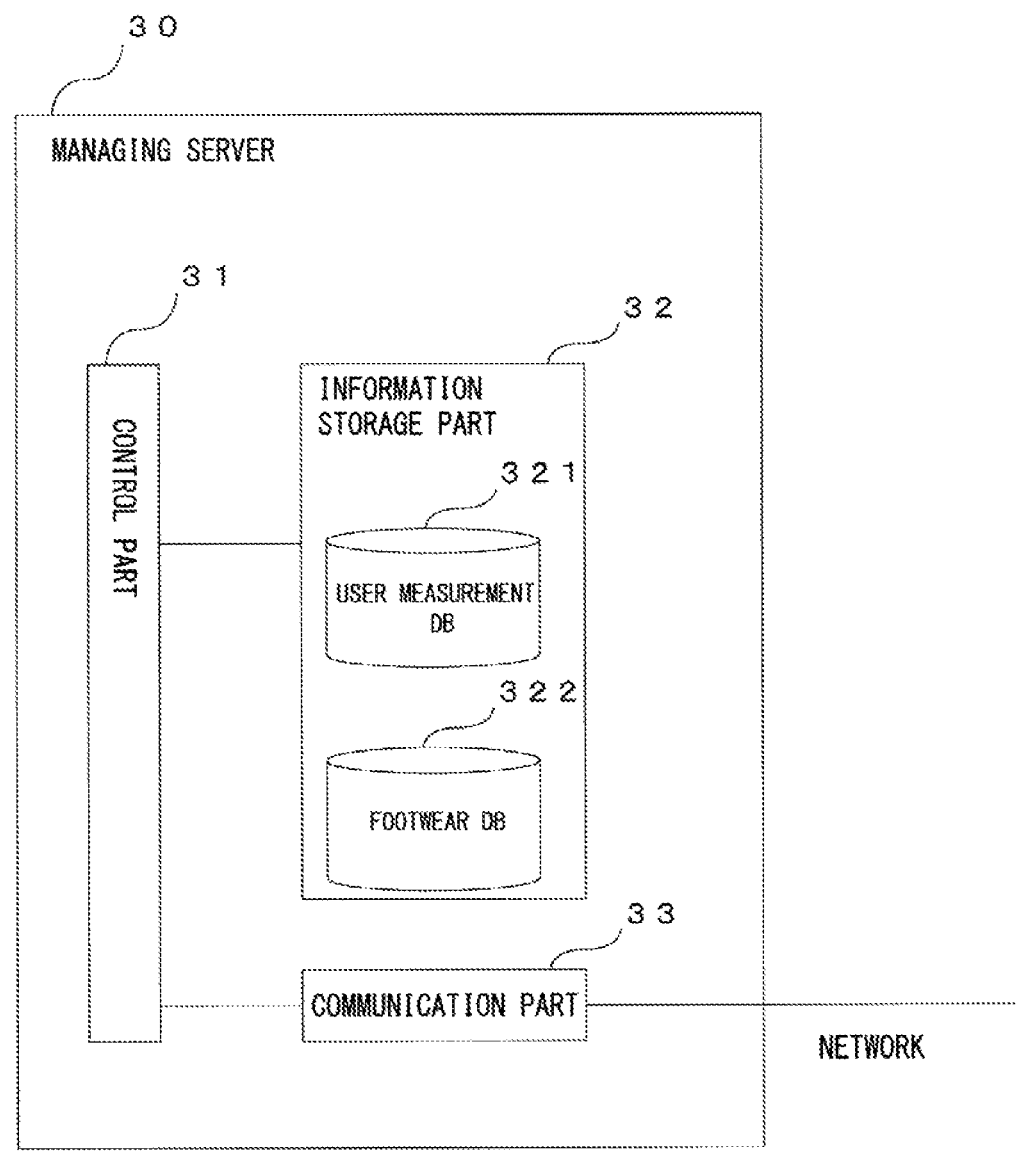
FIG. 15 is a block diagram showing a configuration of a managing server in accordance with the first embodiment of the present invention.

FIG. 15 is a block diagram showing a configuration of the managing server 30 in accordance with the first embodiment of the present invention.

As shown in the drawing, the managing server 30 is constituted by a control part 31 that is constituted by a CPU or the like for controlling the entire managing server 30, an information storage part 32 for storing user measurement information, footwear information and the like, and a communication part 33 that communicates with the user terminal 20 through a network such as the Internet, LAN or the like.

The information storage part 32 of the managing server 30 stores a user measurement DB 321 that is a database for managing user measurement information while being made associated with a user ID for identifying the user, and a footwear DB322 that is a database for managing the size information of footwear, while being made associated with a footwear ID for identifying the footwear.

As the user measurement information managed by the user measurement DB321, examples include information of the respective types of size information fd1 to fd4 and fd21 to fd24 of the user's foot and the pressure distribution (grounding map) information measured by the aforementioned respective measuring sensors 1501 to 1511 and 1521 to 1524, or the like.

The footwear DB322 manages size information of each footwear corresponding to the above-mentioned pieces of size information fd1 to fd4 and fd21 to fd24.

FIG. 16 is a view showing one example of a data configuration of the user measurement DB321 in accordance with the first embodiment of the present invention.

In the user measurement DB321, the pieces of size information fd1, fd2, fd3, fd4, fd21, fd22, fd23, fd24 . . . (information less than fd21 is omitted in the drawing) are registered.

Moreover, although not shown in the example of FIG. 16, the grounding map information or the like is also registered in the user measurement DB321 for each of the users, as described above.

Moreover, in the footwear DB322, size information of footwear measured by a predetermined method and the other information relating the footwear (such as the shape, color, design, kinds, maker, prices, image information, URL of sales page of the footwear in online shops, or the like) are registered, while being made associated with the footwear ID.

FIG. 17 is a view showing one example of a data configuration of the footwear DB322 in accordance with the first embodiment of the present invention.

In the footwear DB322, the pieces of size information fd1, fd2, fd3, fd4, fd21, fd22, fd23, fd24 . . . (information less than fd21 is omitted in the view) are registered.

Moreover, the retrieval range for each piece of the size information is also registered. In the retrieval range, numeric values corresponding to the size information are also registered. For example, size information fd1 of a footwear ID "0001" is "26.4", and since its retrieval range is "26.0 to 26.8" shown in parentheses, the managing server 30 determines that the corresponding footwear is possibly suitable for users having the size information fd1 within the range of "26.0 to 26.8".

Furthermore, although not shown in the example of FIG. 17, various pieces of information relating to the footwear are also registered in the footwear DB322 for each footwear.

The managing server 30 retrieves footwear whose size information is included within the retrieval range of footwear size information corresponding to the size information of the user's foot in the user measurement information, and when such a footwear has been retrieved, determines that the corresponding footwear is suitable for the size and shape of the user's foot.

When the managing server 30 has received user measurement information from the user terminal 20, the control part 31 registers the received user measurement information in the user management DB321.

Moreover, the control part 31 refers to the footwear database DB322, and retrieves footwear that is suitable for the size information included in the user measurement information registered in the above-mentioned user measurement DB321, and transmits information (footwear retrieval result information) of the retrieval results to the user terminal 20.

Upon receipt of the footwear retrieval result information from the managing server 30, the user terminal 20 displays the received footwear retrieval result information on the display part 24.

In this case, as the footwear retrieval result information, for example, a footwear that is coincident with the size and shape of the user's foot measured in the user measurement information transmitted from the user terminal 20 to the managing server 30 or a footwear that is close to the size and shape within a predetermined value range is displayed.

The user is allowed to browse the displayed retrieval result information and also to recognize information of footwear that is suitable for the foot of himself or herself, and refer it at the time of purchasing footwear.

[3] Operations of First Embodiment

Next, the following description will explain measuring operations of the size of the user's foot or the like by the use of the body measuring system in the first embodiment of the present invention.

Figure 18:
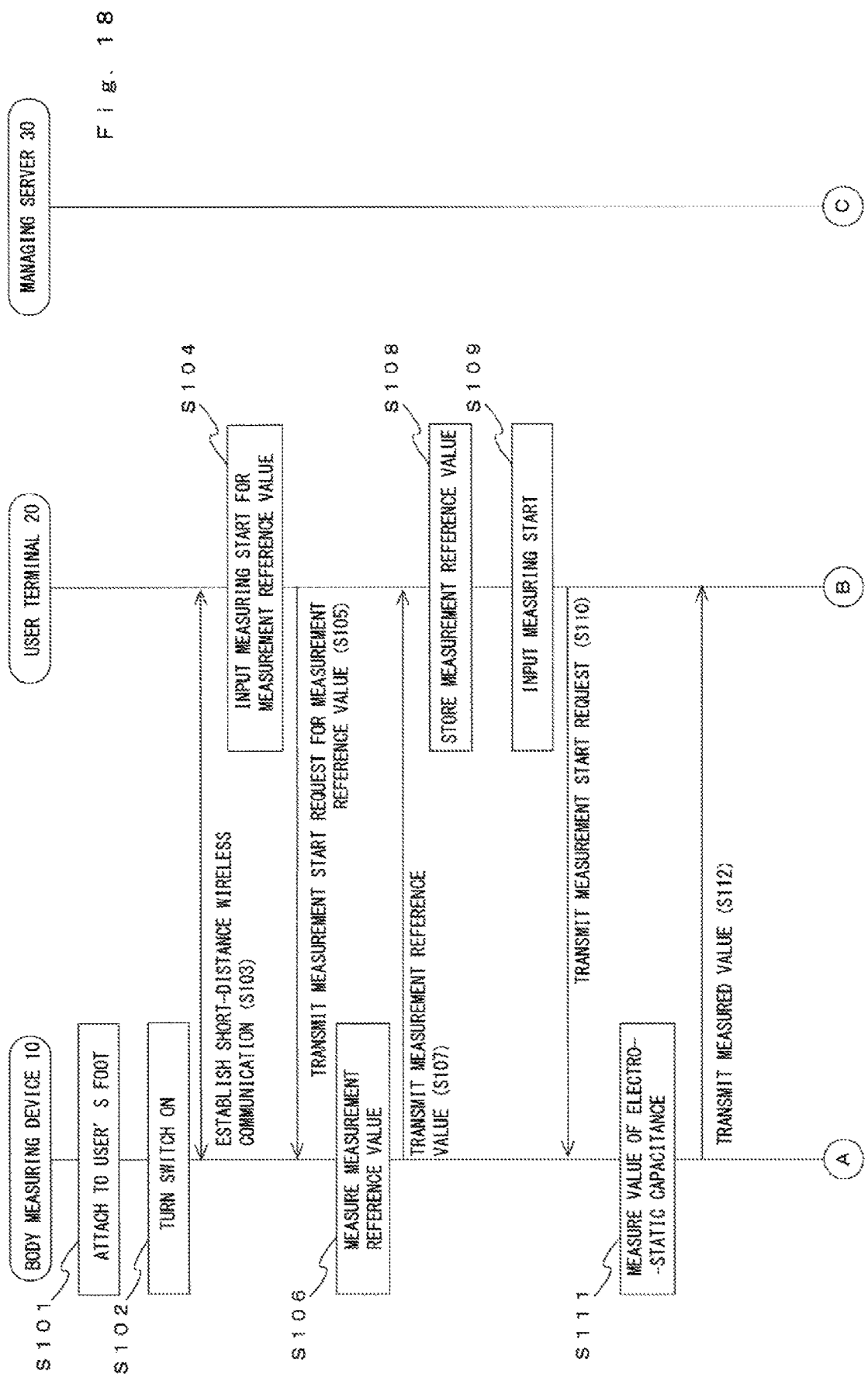
FIG. 18 is a sequence chart showing a flow of measuring operations of a foot size or the like of a user by using the body measuring system in accordance with the first embodiment of the present invention.
Figure 19:
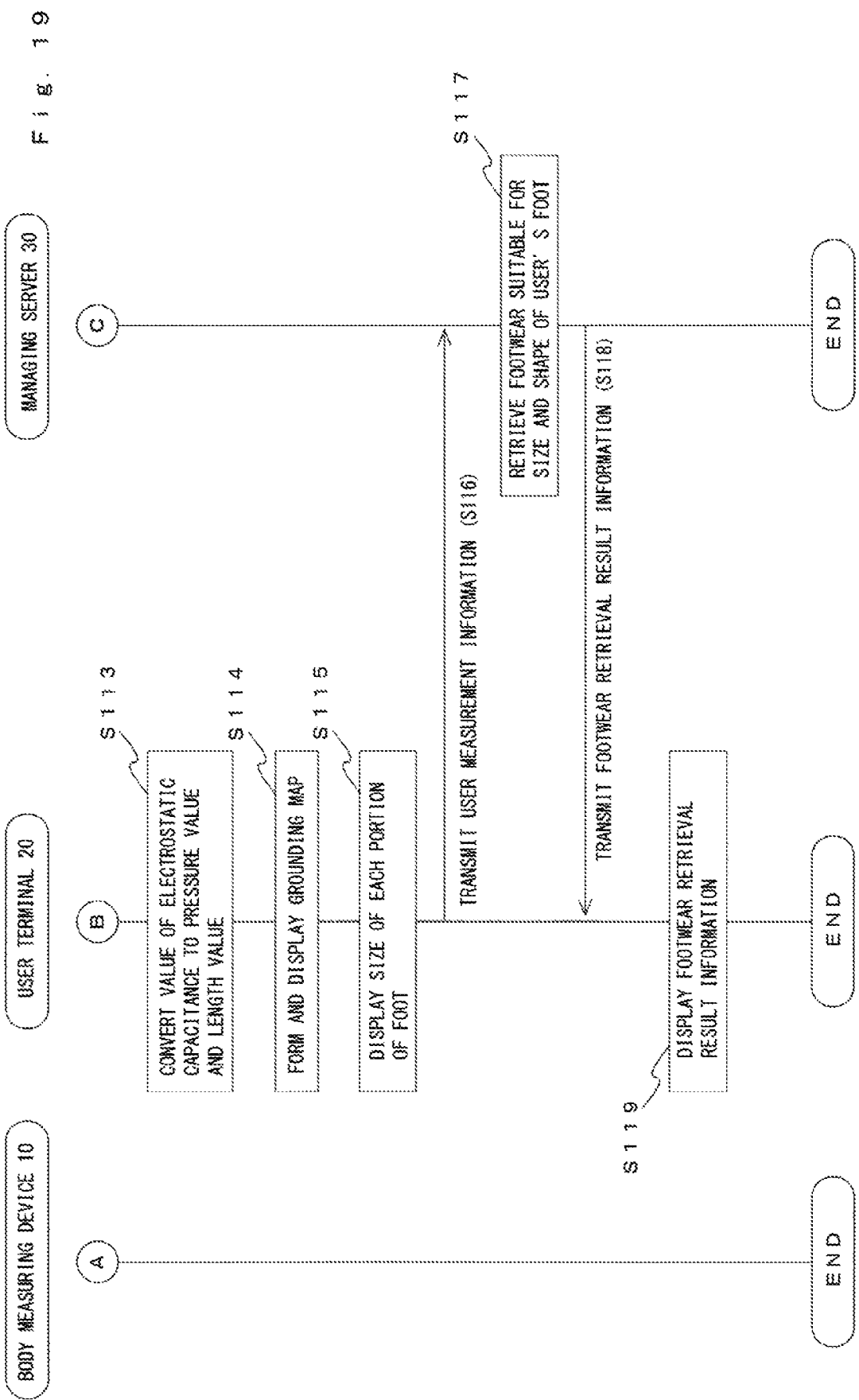
FIG. 19 is a sequence chart showing a flow of measuring operations of a foot size or the like of a user by using the body measuring system in accordance with the first embodiment of the present invention.

FIG. 18 and FIG. 19 are sequence charts showing a flow of measuring operations for the size or the like of a user's foot by the use of the body measuring system in the first embodiment of the present invention.

Referring to the present drawing, the explanation of the measuring operations is carried out.

First, the user puts on a socks state body measuring device 10 so as to attach it onto a foot of himself or herself (step S101).

Next, when the user operates a predetermined switch (not shown) of the body measuring device 10 to turn it ON (step S102), short-distance wireless communication between the body measuring device 10 and the user terminal 20 is established (step S103).

With respect to the establishing method for short-distance wireless communication, any conventional technique may be used, and the detailed description thereof will be omitted.

When the short-distance wireless communication is established between the body measuring device 10 and the user terminal 20, the user operates the operation part 25 of the user terminal 20, with the foot with the footwear attached thereon being raised from the floor so as not to be grounded, and a measuring reference value for starting the measurement is inputted (step S104).

The measuring reference value refers to a measured value of electrostatic capacitance of each of the pressure-type measuring sensors 1506 to 1511 in the state where the user is not grounded.

When the measuring reference value for starting the measurement is inputted thereto as described above, the user terminal 20 transmits a measuring start request of the measuring reference value to the body measuring device 10 (step S105).

Upon receipt of the measuring start request of the measuring reference value from the user terminal 20, the body measuring device 10 measures the measuring reference value of each of the pressure-type measuring sensors 1506 to 1511 without being grounded on the floor (step S106) so that the measuring reference value thus measured is transmitted to the user terminal 20 (step S107).

When the user terminal 20 has received the information of the measuring reference value measured by each of the measuring sensors 1506 to 1511, the control part 21 converts the received measuring reference value (electrostatic capacitance) to a pressure value based upon data indicating correspondence between the electrostatic capacitance and the pressure value, and once stores this value in the information storage part 22 as the reference value (pressure reference value) of the pressure of the sole (step S108).

Next, the user operates the operation part 25 of the user terminal 20, with the foot of himself or herself being grounded on the floor, so as to start measurements (step S109).

Then, the user terminal 20 transmits a measuring start request to the body measuring device 10 (step S110).

Upon receipt of the measuring start request from the user terminal 20, the body measuring device 10 measures the value of electrostatic capacitance of each of the measuring sensors 1501 to 1511 and 1521 to 1524, in the grounded state (step S111), and transmits the measured value to the user terminal 20 (step S112).

When the user terminal 20 has received the measured value of electrostatic capacitance of each of the above-mentioned measuring sensors 1501 to 1511 and 1521 to 1524, the control part 21 converts the value of electrostatic capacitance thus received into the expanded length of the measuring sensor and the pressure value based upon data indicating correspondence between the electrostatic capacitance and the length of the measuring sensor or the pressure value applied to the measuring sensor, and of these, subtracts the pressure reference value from the converted pressure value (step S113).

That is, by taking a difference between the pressure value with the user's foot being grounded and the pressure value without the user's foot being grounded, the value of the corresponding difference is set to a final pressure value applied from the sole of the user.

Next, based upon the value of the length indicated by the electrostatic capacitance of each of the measuring sensors 1501 to 1505 and 1521 to 1524, and the final pressure value of each of the measuring sensors 1506 to 1511, the control part 21 forms a grounding map of the sole of the user and specifies the shape of the user's foot so that the shape is displayed on the display part 24 (step S114).

Next, based upon the shape of the user's foot indicated by the grounding map, the control part 21 calculates each of the values (fd1 to fd4, fd21 to fd24, or the like) of the respective portions of the corresponding foot, and displays the values on the display part 24 (step S115).

In this case, the values of the sizes of the respective portions may be displayed on the display part 24 in an superposed manner with the grounding map.

The user can browse the grounding map and the values of the sizes of the respective portions of the foot displayed on the display part 24 so that the size and shape of himself or herself can be easily confirmed.

Next, the user operates the operation part 25 of the user terminal 20, and transmits the above-mentioned user measurement information including the size and shape of the user's foot to the managing server 30 (step S116).

Upon receipt of the user measurement information from the user terminal 20, the managing server 30 registers the received user measurement information in the user measurement DB321, and also refers to the footwear DB322 so as to retrieve footwear that is suitable for the conditions of the user size information contained in the registered user measurement information (step S117).

In this case, as the retrieving method for the footwear, the control part 31 of the managing server 30, for example, retrieves such a footwear as to be located within a retrieving range in which in the user measurement information, each of the pieces of the size information fd1, fd2, ... is located within a plus/minus predetermined value from each of the pieces of the size information fd1, fd2, ... of the footwear.

For example, with respect to a footwear having a footwear ID "S0001", its size information fd1 is "26.4", and its retrieving range is "26.0 to 26.8". In this case, to the user terminal 20 of users having the size information fd1 within the range "26.0 to 26.8", the retrieval result information including the corresponding footwear is transmitted.

In the present retrieval, the control part 31 desirably extracts any footwear located within the range of all the pieces of the size information fd1, fd2, . . . from the footwear DB322; however, in the case when no such footwear exists, some footwear whose partial size information is located within the range can be extracted, and the managing server 30 may provide the retrieval result information including the information of the corresponding footwear to the user side.

Additionally, with respect to the numeric value width of the retrieving range, the width of any retrieving range may be set depending on each piece of the size information fd1, fd2, fd3, . . . , or the width may be set depending on materials for each footwear.

Next, the control part 31 of the managing server 30 transmits footwear retrieval result information including the retrieval results to the user terminal 20 (step S118).

Upon receipt of the footwear retrieval result information, the user terminal 20 displays the information on the display part 24 (step S119).

For example, as the contents of the footwear retrieval result information displayed on the display part 24 of the user terminal 20, detailed information including a list of footwear having a retrieving range in which user's size information is suitably located, prices, makers, image or the like thereof is displayed.

Moreover, in the footwear retrieval result information, a URL of a Web page of an online shop for use in purchasing the displayed footwear is embedded so that when an icon on the footwear retrieval result information is clicked or the like, the user terminal 20 transmits a user page acquiring request for the Web page for use in purchasing the corresponding footwear to a Web server (or the managing server 30 may be used), and upon receipt of the corresponding page from the Web server, the resulting page is displayed, and thereafter, the corresponding footwear can be purchased on the online shop.

After the above-mentioned processes, the operations are completed.

[4] Summary of the First Embodiment

As described above, in accordance with the body measuring system of the first embodiment of the present invention, by using a simple operation in which the body measuring device 10 is attached to a foot as if to put on socks, based upon the change amount or the like of the electrostatic capacitance of the expansion-type and the pressure-type measuring sensors 1501 to 1511 and 1521 to 1524, the size and shape of the foot can be specified so that it becomes possible to easily confirm the shape of the sole and also to easily retrieve footwear that fits to the foot.

Moreover, freely expandable materials are used for the respective measuring sensors 1501 to 1511 and 1521 to 1524 of the body measuring device 10; therefore, when the user removes the body measuring device 10 as if to take off socks, the shape thereof is recovered so that the size or the like of a foot can be measured any number of times.

[5] Modified Example of First Embodiment (1) Management of Database for Pressure Reference Value by Managing Server 30

In the above-mentioned first embodiment, the body measuring device 10 measures a measuring reference value, with a foot being raised from the floor, and based upon the measuring reference value, the user terminal 20 generates a pressure reference value so as to be stored; however, in the present modified example, the user terminal 20 is designed to receive the pressure reference value from the managing server 30 through a network at the time of a measuring process.

In the present modified example, the managing server 30 makes the respective pressure reference values of the measuring sensors of the respective body measuring devices 10 associated with a measuring device ID for identifying each of the body measuring devices 10 individually so as to be managed by a database stored in the information storage part 32.

When at the time of starting measurements, communication such as short-distance wireless communication or the like has been established with the body measuring device 10, the user terminal 20 receives measuring device IDs for identifying the respective body measuring devices 10 individually from the body measuring devices 10.

Moreover, the user terminal 20 transmits the measuring device IDs received from the body measuring devices 10 to the managing server 30.

Upon receipt of the corresponding measuring device IDs from the user terminal 20, the managing server 30 refers to the database, and extracts the pressure reference value that is made correspondence with the measuring device ID, and transmits it to the user terminal 20.

Upon receipt of the pressure reference value of each of the measuring sensors of the corresponding body measuring device 10 from the managing server 30, the user terminal 20 carries out measurements in the same manner as in the first embodiment by using the received pressure reference value.

In this manner, in the present modified example, the managing server 30 preliminarily manages the pressure reference value by the database for each of the measuring sensors of body measuring device 10, and since the user terminal 20 carries out measurements of the size or the like of the body by using the pressure reference value, the user is allowed to easily carry out the measurements without the necessity of having to make an action such as to once raise the foot from the floor.

(2) Management by Managing Server 30 of Data Indicating Correspondence between Electrostatic Capacitance and Length of Measuring Sensor or Pressure Value Applied to Measuring Sensor In the above-mentioned first embodiment, in the explanation of operations of step S113, when the user terminal 20 has received the measuring value of electrostatic capacitance of each of the measuring sensors 1501 to 1511 and 1521 to 1524, the control part 21 converts the received value of the electrostatic capacitance into the expanded length of the measuring sensor and the pressure value based upon data indicating correspondence between the electrostatic capacitance and the length of the measuring sensor or the pressure value applied to the sensor.

In the present modified example, in place of the user terminal 20, the managing server 30 stores the data indicating correspondence between the electrostatic capacitance and the length of the measuring sensor or the pressure value applied to the sensor.

Upon receipt of data of the measured value of electrostatic capacitance by the measuring sensor from the body measuring device 10, the user terminal 20 transmits the data of the measured value of the electrostatic capacitance to the managing server 30.

When the managing server 30 has received the data of the measured value of the electrostatic capacitance from the user terminal 20, the control part 31 of the managing server 30 converts the received value of the electrostatic capacitance into the expanded length of the measuring sensor and the pressure value based upon data indicating correspondence between the electrostatic capacitance of the measuring sensor and the length of the measuring sensor or the pressure value applied to the sensor.

As described above, the control part 31 of the managing server 30 calculates the pressure reference value and the pressure value based upon the value of the electrostatic capacitance as well as based upon the data indicating correspondence between the electrostatic capacitance of the measuring sensor and the length of the measuring sensor or the pressure value applied to the measuring sensor, and by taking a difference therebetween, calculates the value of the difference as the final pressure value from the sole of the user.

Thereafter, based upon the value of the length indicated by electrostatic capacitance of each of the measuring sensors 1501 to 1505 and 1521 to 1524 and the final pressure value of each of the measuring sensors 1506 to 1511, the control part 31 of the managing server 30 generates data of a grounding map of the sole of the user, and calculates the value of the size of each of the respective portions of the foot (fd1 to fd4, and fd21 to fd24 or the like) so that the communication part 33 of the managing server 30 transmits the data of the grounding map of the sole of the user and the data of the value of the size of each of the respective portions thereof to the user terminal 20.

Upon receipt of the data of the grounding map of the sole of the user and the data of the values of sizes of the respective portions from the managing server 30, the user terminal 20 displays the data on the display part 24.

In this case, the values of the sizes of the respective portions may be displayed on the display part 24 in a superposed manner with the grounding map.

In this manner, in the present modified example, in place of the user terminal 20, the managing server 30 stores the data indicating correspondence between the electrostatic capacitance of the measuring sensor and the length of the measuring sensor or the pressure value applied to the measuring sensor, and calculates the data of the grounding map of the sole of the user and the data of the values of sizes of the respective portions, and then provides these data to the user terminal 20; therefore, the user terminal 20 does not need to store the associated data in itself so that it becomes possible to simplify the device configuration.

(3) Modified Example of Attaching Position of Measuring Sensor on Foot Bottom Part 2

In the above-mentioned first embodiment, as shown in FIG. 7, the expansion-type or pressure-type measuring sensors 1501 to 1511 are attached onto the foot bottom part 2.

In the present modified example, an expansion-type measuring sensor 1542 is installed at a position different from that of the above-mentioned example.

Figure 20:
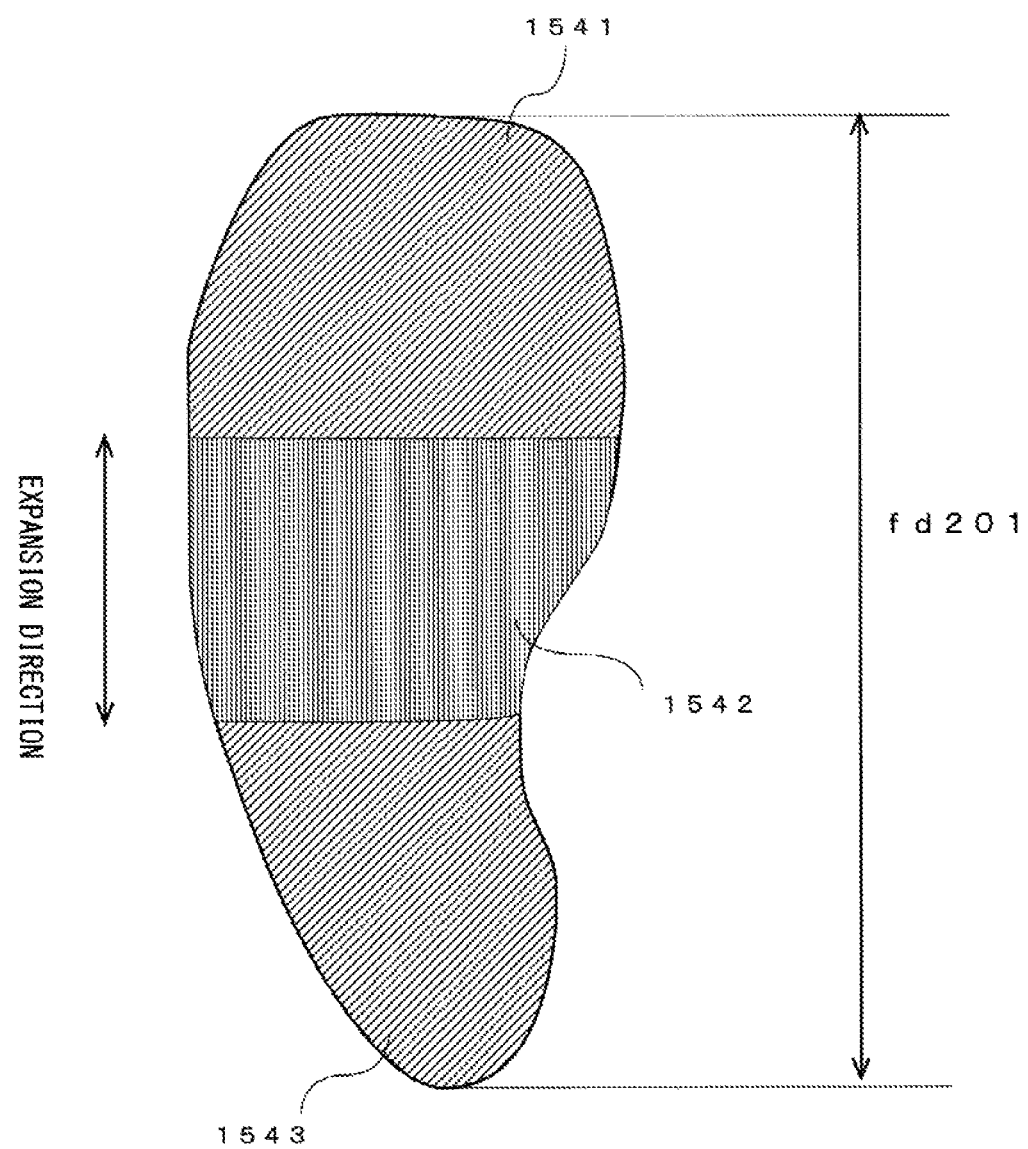
FIG. 20 is a view showing one example of attached positions of measuring sensors on a bottom portion of a left foot of a body measuring device having a footwear shape in a modified example of the first embodiment of the present invention.

FIG. 20 is a view showing one example of an attached position of the measuring sensor on the bottom portion of a left foot of a body measuring device having a footwear shape in a modified example of the first embodiment of the present invention.

In the present modified example shown in the view, on the foot bottom part 2 of the body measuring device 10, non-expansion parts 1541 and 1543 made of a non-expandable material and an expandable measuring sensor 1542 are installed.

As shown in the drawing, the non-expansion part 1541 forms the toe portion of the foot bottom part 2 and the non-expansion part 1543 forms the heel portion of the foot bottom part 2.

The expandable measuring sensor 1542 has its two ends in the foot length direction coupled to the corresponding non-expansion parts 1541 and 1543 so as to be sandwiched between the non-expansion parts 1541 and 1543, and is designed to be expandable in a direction shown in the view.

Additionally, although not shown in the present view, the measuring sensor 1542 is connected to the detection part 14 through wire, and by using the same method as that of the first embodiment, the control part 11 calculates the value of the electrostatic capacitance of the measuring sensor 1542, and based upon the value of the electrostatic capacitance, measures the expanded length of the measuring sensor 1542.

When the user attaches the body measuring device 10 having a footwear shape to his or her own foot, the measuring sensor 1542 expands in the expanding direction (foot length direction) of FIG. 20.

In this case, supposing that the length in the foot length direction from the toe portion to the heel portion of the foot bottom part 2, without being attached to the user, is fd201, and that the extended length of the measuring sensor 1542 caused by being attached to the user is fd202, the length of the entire foot bottom part 2 after being attached to the user is represented by (fd201+fd202).

The user terminal 20 has the value of the length fd201 in the foot length direction of the foot bottom part 2 preliminarily stored in the information storage part 22, or receives the corresponding value from the body measuring device 10, the managing server 30 or the like, and stores the value therein.

When the user attaches the body measuring device 10 to his or her foot and measures the expanded length fd202 of the measuring sensor 1542, the user terminal 20 adds the corresponding expanded length fd202 and the preliminarily acquired entire length fd201 to each other, and calculates the entire length of the foot bottom part 2 at the time when the body measuring device 10 is attached.

In this manner, by forming only the one portion of the foot bottom part 2 of the body measuring device 10 by using the expansion-type measuring sensor 1542, with the other portions being formed as the non-expansion parts 1541 and 1543 by using comparatively inexpensive non-expandable materials (cloth material, fibers), the manufacturing costs of the body measuring device 10 can be greatly reduced.

Moreover, by forming one portion of the foot bottom part 2 with a non-expandable material, the strength of the foot bottom part 2 can be maintained at a predetermined level or more so that it is possible to prevent the occurrence of a deformation or the like.

Additionally, in the present modified example, for example, only the arch portion of the foot bottom part 2 is constituted by the expansion-type measuring sensor 1542 and the other portions (toe portion and heel portion) are constituted by using a non-expandable material (non-expansion parts 1541 and 1543); however, the layout position of the expansion-type measuring sensor is not intended to be limited by the arch portion, and the layout position of the non-expandable material is not intended to be limited by the toe portion and the heel portion. For example, only the heel portion may be formed by using the expansion-type measuring sensor, while the other portions may be formed by using the non-expandable material.

(4) Configuration of Measuring Sensor

In the above-mentioned first embodiment, the measuring sensor is formed by using a three-layer structure in which a dielectric film is disposed between two electrodes.

In the present modified example, the sensor is formed by using a structure having three or more layers in which between paired electrodes, a dielectric film is disposed to form such an arrangement where electrode, dielectric film, electrode, dielectric film, electrode, . . . , etc. are sequentially stacked. In this configuration also, the respective electrodes are connected to the detection part 14 through wires.

Second Embodiment

[1] Outline of Second Embodiment

In the first embodiment, the respective measuring sensors are designed to measure the pressing force and the degree of extension of the body measuring device 10 based upon a change in the electrostatic capacitance.

The measuring sensor may be designed to measure the pressing force and the extension of the body measuring device 10 based upon a change in another characteristic other than the electrostatic capacitance so as to specify the size and shape of the body of the user.

In the following description, unless otherwise specified, the same configuration as that of the first embodiment is used, and an explanation will be given on a measuring sensor for measuring electric resistance as one example of the change in characteristics.

[2] Configuration of Second Embodiment (1) Configuration of Pressure-Type Measuring Sensor FIG. 21 is an exploded view showing one example of a configuration of a pressure-type measuring sensor for use in a body measuring device 10 in accordance with a second embodiment of the present invention.

Figure 22:
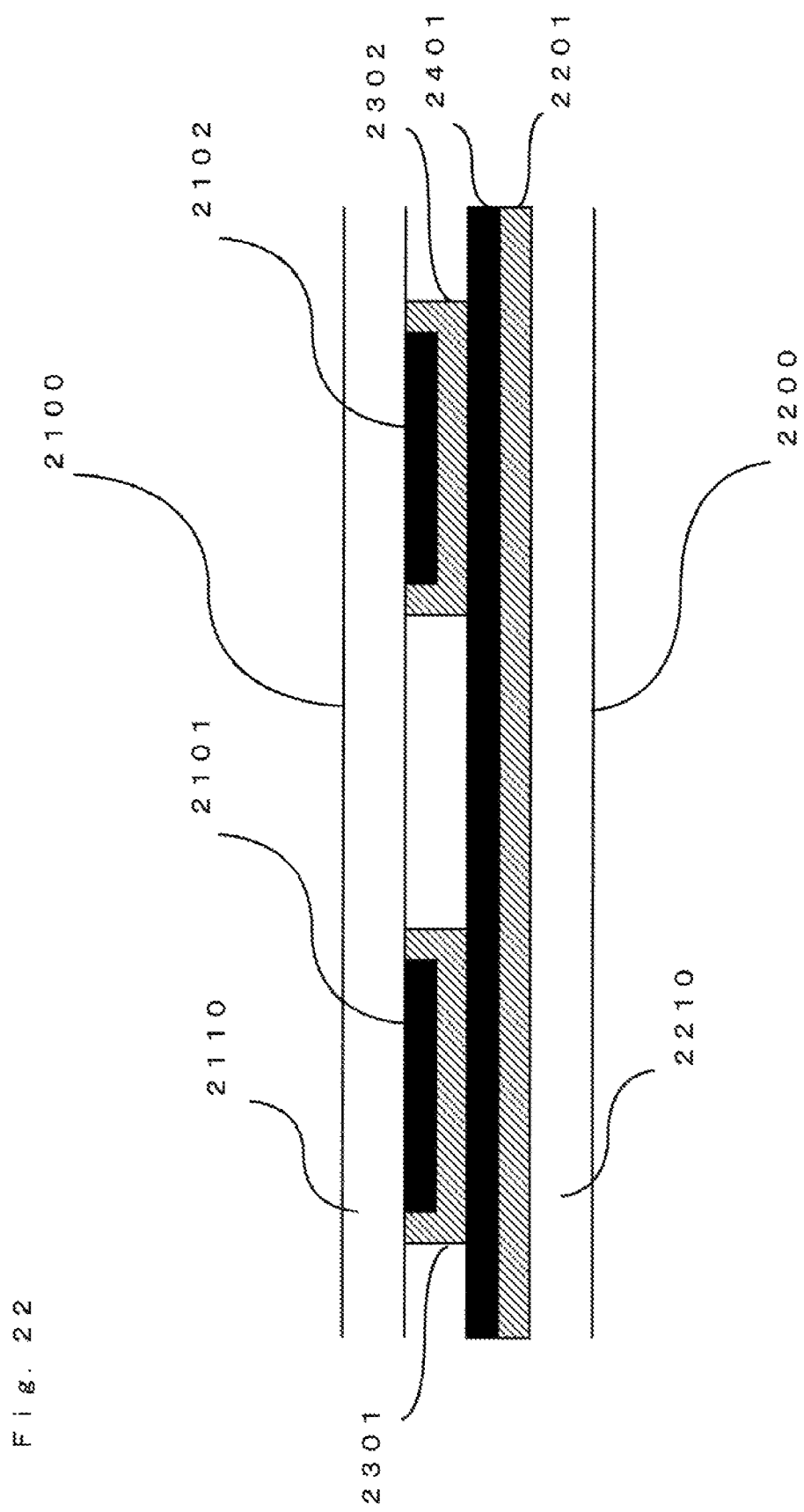
FIG. 22 is a cross-sectional side view showing a configuration of a pressure-type measuring sensor in accordance with the second embodiment of the present invention.

FIG. 22 is a cross-sectional side view showing a configuration of a pressure-type measuring sensor in accordance with the second embodiment of the present invention.

As shown in the drawings, the pressure-type measuring sensor in accordance with the present embodiment is provided with a pair of electrode substrates 2100 and 2200 whose electrodes are made face to face with each other.

The electrode substrate 2100 is constituted by a film base member 2110, a plurality of electrodes 2101 to 2107 disposed substantially in parallel with one another on the film base member 2110, and conductive pressure-sensitive members 2301 to 2307 that cover the opposed sides of the electrodes 2101 to 2107.

The electrode substrate 2200 is constituted by a film base member 2210, a plurality of electrodes 2201 to 2207 disposed substantially in parallel with one another on the film base member 2210, and conductive pressure-sensitive members 2401 to 2407 that cover the opposed sides of the electrodes 2201 to 2207.

The electrode substrates 2100 and 2200 are designed so that the electrodes 2101 to 2107 and the electrodes 2201 to 2207 are arranged so as to intersect with each other and bonded to each other, with the result that between the electrodes 2101 to 2107 and the electrodes 2201 to 2207, the pressure-sensitive members 2301 to 2307 as well as 2401 to 2407, are interposed.

In the pressure-sensitive members 2301 to 2307 and 2401 to 2407, a conductive substance and a non-conductive substance are contained.

Examples of the conductive substance include metal (silver, copper, aluminum, or the like) and a material containing a silicon-based or a carbon-based substance, and examples of the non-conductive substance include a polyester-based resin, a polyurethane-based resin or a polyamide-based resin.

Moreover, the pressure-sensitive members 2301 to 2307 and 2401 to 2407 may be formed by applying an ink containing the above-mentioned conductive substance and non-conductive substance onto the opposed surfaces of the paired electrodes 2101 to 2107 and 2201 to 2207.

On the surfaces on the opposed sides of the pressure-sensitive members 2301 to 2307 and 2401 to 2407, particulate conductive substance and non-conductive substance protrude to form concavo-convex portions, and in a state where no pressure is applied onto the intersecting portions between the electrodes 2101 to 2107 and the electrodes 2201 to 2207, non-contact portions remain on the mutual surfaces of the pressure-sensitive members 2301 to 2307 and 2401 to 2407.

In the case when a pressure is applied to each of the intersecting portions, since the contact area between the surfaces of the pressure-sensitive members 2301 to 2307 and 2401 to 2407 is substantially increased, the resistance value of the contact intersecting portions is reduced.

The measuring sensor is provided with a measuring device for measuring the resistance value at the intersecting portions between the corresponding electrodes 2101 to 2107 and 2201 to 2207, and the plural electrodes 2101 to 2107 and 2201 to 2207 are coupled to the measuring device through wires.

(2) Configuration of Expansion-type Measuring Sensor

In the present embodiment, the expansion-type measuring sensor is constituted by synthetic fibers having expandability, formed by mixedly fabricating conductive fibers and non-conductive fibers, and a measuring device for measuring the resistance value between the two ends in the expansion/contraction direction (distance-measuring direction) of the synthetic fibers.

Examples of the conductive fibers include carbon fibers, metal fibers (silver, copper, aluminum or the like), fibers formed by a conductive polymer, or conductive polymer fibers containing a conductive material (conductive filler), or metal coating fibers (silver, copper, aluminum or the like), or mixtures thereof.

Examples of the non-conductive fibers include polyester-based fibers, polyurethane-based fibers, polyamide-based fibers, cotton. or the like.

Additionally, metal coating fibers or fibers or the like containing a conductive material (conductive filler) may be solely used, without being mixedly fabricated with non-conductive fibers.

When a tension is applied to the expansion-type measuring sensor to be expanded in the expansion/contraction direction, the length of the measuring sensor itself becomes longer, with the cross-sectional area in a direction perpendicular to the expansion direction being made smaller, with the result that the electric resistance is increased.

Based upon a change in the electric resistance value of the expansion-type measuring sensor, the body measuring device 10 measures the amount of change in the length of the measuring sensor.

[3] Operations of Second Embodiment (1) Operations of Pressure-type Measuring Sensor At the time of measuring a pressure applied to the measuring sensor by using the pressure-type measuring sensor in accordance with the present embodiment, the measuring device applies a voltage between the electrodes 2101 to 2107 and the electrodes 2201 to 2207, and measures the resistance value at each intersecting portion between the electrodes 2101 to 2107 and the electrodes 2201 to 2207.

The body measuring device 10 transmits the resistance value at the intersecting portion of the electrodes of the measuring sensor thus measured to the user terminal 20.

The user terminal 20 stores data indicating correspondence between the resistance value at the intersecting portion of the electrodes 2101 to 2107 and the electrodes 2201 to 2207 of the measuring sensor and the numeric value of the pressure applied to the intersecting portion, and data indicating the positional information (coordinates) of the intersecting portion of the corresponding electrodes.

Upon receipt of the resistance value of each of the intersecting portions of the above-mentioned electrodes from the body measuring device 10, the user terminal 20 converts the received resistance value into the pressure value at the intersecting portion of the electrodes, and also specifies the position of the intersecting portion subjected to the pressure, based upon the corresponding data.

The present embodiment makes it possible to specify the shape and size of the sole of the user by using the pressure-type measuring sensor in the same manner as in the first embodiment.

(2) Operations of Expansion-type Measuring Sensor

In the above-mentioned measuring device, when the user has attached the body measuring device 10 to his or her body and the synthetic fibers are expanded, the contact portions between the conductive fibers are separated so that the resistance value of the synthetic fibers is increased. By measuring the amount of an increase, the measuring sensor makes it possible to specify the degree of expansion of the synthetic fibers.

The body measuring device 10 transmits the resistance value of the measured synthetic fibers to the user terminal 20.

The user terminal 20 stores data indicating correspondence between the resistance value of the synthetic fibers and the length in the expanding direction of the synthetic fibers, and upon receipt of the resistance value of the synthetic fibers from the body measuring device 10, converts the received resistance value into the length of the synthetic fibers based upon the corresponding data.

The user terminal 20 has stored data indicating correspondence between the resistance value of the synthetic fibers formed by mixedly fabricating the conductive fibers and non-conductive fibers and the value of the length in the expansion/contraction direction thereof, and data indicating the positional information (coordinates) of the measuring sensor provided with the corresponding synthetic fibers.

Upon receipt of the resistance value of the synthetic fibers from the body measuring device 10, the user terminal 20 converts the received resistance value to the length of the synthetic fibers, and specifies the position of the measuring sensor provided with the synthetic fibers based upon the corresponding data.

The present embodiment makes it possible to specify the shape and size of the sole of the user and the size of the circumference thereof by using the expansion-type measuring sensor, in the same manner as in the first embodiment.

[4] Summary of the Second Embodiment

As described above, since the body measuring system in accordance with the second embodiment of the present invention measures the resistance value of the measuring sensor, and the pressure of the sole of the user and the length of the synthetic fibers installed in the measuring sensor are detected based upon the resistance value, it becomes possible to easily specify the size and shape of the user's foot.

Summary of Embodiments

As described above, in accordance with the body measuring system of the first embodiment of the present invention, by using a simple operation in which the body measuring device 10 is attached to a foot as if to put on socks, and based upon a change in characteristics of expansion-type and pressure-type measuring sensors (amount of change or the like of the electrostatic capacitance or the resistance value), the size and shape of the foot can be specified so that it becomes possible to easily confirm the shape of the sole, and also to retrieve footwear that fits to the foot.

The above-mentioned body measuring device 10, the user terminal 20 and the managing server 30 can be realized by programs mainly loaded into the CPU and memory. However, this device or server can be constituted by a combination of other arbitrary hardware and software, and its high degree of freedom of designing has been easily understood by the person skilled in the art.

Moreover, in the case when the above-mentioned body measuring device 10, user terminal 20 or managing server 30 is constituted as a group of modules, these programs may be recorded on a recording medium, such as an optical recording medium, a magnetic recording medium, a magneto-optical recording medium, a semiconductor or the like so as to be loaded from the recording medium, or may be loaded from an external apparatus connected through a predetermined network.

Additionally, the above-mentioned embodiments are merely examples of desirable embodiments of the present invention, and the embodiments of the present invention are not intended to be limited thereby, and various modifications may be made therein within the scope without departing from the gist of the present invention.

For example, based upon electrostatic capacitance, the measuring sensor in the first embodiment of the present invention specifies the shape and size of the user's body (foot), and based upon resistance value, the measuring sensor in the second embodiment specifies those of the user's body (foot); however, those may be specified based upon a change in another electrical characteristic.

Moreover, with respect to the configuration for measuring the electrostatic capacitance or the resistance value by the measuring sensor, any of various known techniques not described in the present specification may be applied thereto.

Moreover, in the above-mentioned embodiments, the measurements are started when the user operates the user terminal 20; however, the measurements may be designed to be started when the user operates a predetermined switch or the like attached to the body measuring device 10.

EXPLANATION OF REFERENCE NUMERALS

1 main body part
2 foot bottom part 3 insertion opening part
4 measurement processing part
10 body measuring device
11, 21, 31 control part
12, 22, 32 information storage part
13, 23, 33 communication part
14 detection part
15 measuring part
20 user terminal
24 display part
25 operation part
30 managing server
100 base member
321 user measurement DB
322 footwear DB
1000, 1100, 1200, 1501 to 1511, 1521 to 1524, 1542 measuring sensor
1001, 1201 dielectric film
1002, 1003, 1121 to 1127, 1131 to 1137, 1202, 1203, 2101 to 2107, 2201 to 2207 electrode
1110 dielectric film substrate
1120, 1130, 2100, 2200 electrode substrate
1141 to 1147, 1151 to 1157 wire
1541, 1543 non-expansion part
2110, 2210 film base member
2301 to 2307, 2401 to 2407 pressure-sensitive member

The invention claimed is:

1. A body measuring device which, when attached to a user, specifies a size and shape of a foot of the user, comprising:
a measuring sensor for measuring a physical change amount based upon a change in electrical characteristics, wherein the measuring sensor includes a pressure-type measuring sensor for measuring a pressure applied from a sole of the user and an expansion-type measuring sensor for measuring a degree of expansion of a base member caused by the shape of the foot of the user wherein the body measuring device is formed into a footwear shape, and the expansion-type measuring sensor is formed into an expandable belt shape, and is characterized in that a non-expandable member is coupled to a tip of the expansion-type measuring sensor so as to form a sole portion.

2. A body measuring device which, when attached to a user, specifies a size and shape of a foot of the user, comprising:
a measuring sensor for measuring a physical change amount based upon a change in electrical characteristics, wherein the measuring sensor includes a pressure-type measuring sensor for measuring a pressure applied from a sole of the user and an expansion-type measuring sensor for measuring a degree of expansion of a base member caused by the shape of the foot of the user wherein the body measuring device is formed into a footwear shape, and the expansion-type measuring sensor is formed into a belt shape expandable in a foot length direction, and is characterized in that non-expandable members are coupled to two ends in a foot length direction of the expansion-type measuring sensor so as to form a sole portion.

3. The body measuring device according to claims 1 or 2, wherein the body measuring device is formed into a footwear shape, and the pressure-type measuring sensor is disposed on a portion of the sole, and is characterized by measuring a pressure that is exerted on the sole of the user in a gravity direction.

4. The body measuring device according to claims 1 or 2, wherein the body measuring device is formed into a footwear shape, and the expansion-type measuring sensor is disposed on a toe portion of the sole, and is characterized by measuring a degree of expansion of the base member caused by a length of the toe of the user.

5. The body measuring device according to claims 1 or 2, wherein the body measuring device is formed into a footwear shape and the expansion-type measuring sensor is disposed in a foot-surrounding direction, and is characterized by measuring a degree of expansion of the base member caused by the foot-surrounding length of the user.

6. The body measuring device according to claims 1 or 2, wherein pressure-type measuring sensor includes a pair of electrode substrates on which a plurality of plate-shape electrodes are disposed and a dielectric film disposed between the paired electrode substrates, and is characterized in that when a pressure is applied to the electrodes, a magnitude of a pressure applied from the sole is specified based upon a change in electrostatic capacitance caused by the pressure.

7. The body measuring device according to claims 1 or 2, wherein the pressure-type measuring sensor includes a pair of electrode substrates on which a plurality of plate-shape electrodes are disposed substantially in parallel with one another and a pressure sensitive member containing a conductive substance, and the paired electrode substrates are disposed so as to allow the respective electrodes to be made face to face with each other, and the pressure sensitive member coats the opposed surfaces of the paired electrode substrates so that when a pressure is applied to an intersecting portion of the electrodes, a magnitude of a pressure applied from the sole is specified based upon a change in electric resistance value caused by the pressure.

8. The body measuring device according to claims 1 or 2, wherein the expansion-type measuring sensor includes a pair of plate-shape electrodes and a dielectric film disposed between the paired electrodes, and is characterized in that when a tension is applied to the electrodes so as to be expanded, the degree of expansion of the electrodes caused by the shape of the user's body is specified based upon a change in electrostatic capacitance caused by the expansion of the electrodes.

9. The body measuring device according to claims 1 or 2, wherein the expansion-type measuring sensor includes a plate-shape electrode having expandability, and is characterized in that when expanded upon application of a tension onto the electrode, the degree of expansion of the electrode caused by the shape of the user's body is specified based upon a change in electrical resistance value caused by the expansion of the electrode.

10. A body measuring system comprising:
the body measuring device according to claims 1 or 2;
a user terminal through which data representing a physical change amount measured by the measuring sensor is acquired from the body measuring device, and
a managing server that is provided with a database for managing a size and shape of a footwear,
wherein when data representing the physical change amount is acquired from the body measuring device, the user terminal transmits the data representing the physical change amount thus acquired to the managing server so that upon receipt of the data representing the physical change amount from the user terminal, the managing server refers to the database and retrieves a footwear that is coincident with the data representing the physical change amount thus received, and transmits the results of retrieval to the user terminal.

11. A body measuring device which, when attached to a user, specifies a size and shape of a foot of the user, comprising:
a measuring sensor for measuring a physical change amount based upon a change in electrical characteristics, wherein the measuring sensor includes an expansion-type measuring sensor for measuring a degree of expansion of a base member caused by the shape of the foot of the user wherein the body measuring device is formed into a footwear shape, and the expansion-type measuring sensor is formed into an expandable belt shape, and is characterized in that a non-expandable member is coupled to a tip of the expansion-type measuring sensor so as to form a sole portion.

12. A body measuring device which, when attached to a user, specifies a size and shape of a foot of the user, comprising:
a measuring sensor for measuring a physical change amount based upon a change in electrical characteristics, wherein the measuring sensor includes a pressure-type measuring sensor for measuring a pressure applied from a sole of the user and an expansion-type measuring sensor for measuring a degree of expansion of a base member caused by the shape of the foot of the user wherein the body measuring device is formed into a footwear shape, and the expansion-type measuring sensor is formed into a belt shape expandable in a foot length direction, and is characterized in that non-expandable members are coupled to two ends in a foot length direction of the expansion-type measuring sensor so as to form a sole portion.

13. The body measuring device according to claims 11 or 12, wherein the body measuring device is formed into a footwear shape, and the expansion-type measuring sensor is disposed on a toe portion of the sole, and is characterized by measuring a degree of expansion of the base member caused by a length of the toe of the user.

14. The body measuring device according to claims 11 or 12, wherein the body measuring device is formed into a footwear shape, and the expansion-type measuring sensor is disposed in a foot-surrounding direction, and is characterized by measuring a degree of expansion of the base member caused by the foot-surrounding length of the user.

15. The body measuring device according to claims 11 or 12, wherein the expansion-type measuring sensor includes a pair of plate-shape electrodes and a dielectric film disposed between the paired electrodes, and is characterized in that when a tension is applied to the electrodes so as to be expanded, the degree of expansion of the electrodes caused by the shape of the user's body is specified based upon a change in electrostatic capacitance caused by the expansion of the electrodes.

16. The body measuring device according to claim 11 or 12, wherein the expansion-type measuring sensor includes a plate-shape electrode having expandability, and is characterized in that when expanded upon application of a tension onto the electrode, the degree of expansion of the electrode caused by the shape of the user's body is specified based upon a change in electrical resistance value caused by the expansion of the electrode.

* * * * *